(12) United States Patent
Wang et al.

(10) Patent No.: US 6,239,173 B1
(45) Date of Patent: *May 29, 2001

(54) 3-PHENYL-4-(4(METHYLSULFONYL) PHENYL)-2-(5H)-FURANONE AS A COX-2 INHIBITOR

(75) Inventors: Zhaoyin Wang, Pierrefond; Michel Therien, Laval, both of (CA)

(73) Assignee: Merck Frosst Canada Inc./Merck Frosst Canada & Co., Kirkland (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 10 days.

This patent is subject to a terminal disclaimer.

(21) Appl. No.: 09/443,000

(22) Filed: Nov. 18, 1999

Related U.S. Application Data

(63) Continuation of application No. 08/672,562, filed on Jun. 28, 1996, which is a continuation of application No. 08/435,060, filed on May 8, 1995, now abandoned, which is a division of application No. 08/179,467, filed on Jan. 10, 1994, now Pat. No. 5,474,995, which is a continuation-in-part of application No. 08/082,196, filed on Jun. 24, 1993, now abandoned.

(51) Int. Cl.[7] .................. A61K 31/365; C07D 307/58

(52) U.S. Cl. ........................... 514/473; 549/323

(58) Field of Search .................. 549/323; 514/473

(56) References Cited

U.S. PATENT DOCUMENTS

| | | |
|---|---|---|
| 3,351,468 | 11/1967 | Forehlich et al. . |
| 3,743,656 | 7/1973 | Brown et al. ............... 549/79 |
| 4,302,461 | 11/1981 | Cherkofsky et al. . |
| 4,321,118 | 3/1982 | Felder et al. ............... 568/336 |
| 4,427,693 | 1/1984 | Haber et al. . |
| 4,432,974 | 2/1984 | Haber et al. . |
| 4,539,332 | 9/1985 | Biftu et al. . |
| 4,585,789 | 4/1986 | Okamoto et al. ............ 514/461 |
| 4,797,417 | 1/1989 | Okamoto et al. ............ 514/473 |
| 4,820,827 | 4/1989 | Haber et al. . |
| 4,853,473 | 8/1989 | Fischer et al. ............. 549/326 |
| 4,855,320 | 8/1989 | Chatterjee et al. ......... 514/473 |
| 4,929,525 | 5/1990 | Kuroda et al. . |
| 4,968,817 | 11/1990 | Brima ........................ 549/313 |
| 5,094,681 | 3/1992 | Kramer et al. ............. 71/88 |
| 5,145,860 | 9/1992 | Takasugi et al. . |
| 5,196,532 | 3/1993 | Wuest et al. ............... 514/319 |
| 5,207,817 | 5/1993 | Kramer et al. ............. 504/289 |
| 5,217,971 | 6/1993 | Takasugi et al. . |
| 5,229,386 | 7/1993 | Takasugi et al. . |
| 5,274,072 | 12/1993 | Weaver et al. ............. 528/354 |
| 5,474,995 | * 12/1995 | Ducharme et al. .......... 514/241 |

FOREIGN PATENT DOCUMENTS

| | | |
|---|---|---|
| 055 470 | 7/1982 | (EP) . |
| 087 629 | 8/1983 | (EP) . |
| 0 274 867 | 7/1988 | (EP) . |
| 317 845 | 11/1988 | (EP) . |
| 388 909 | 3/1990 | (EP) . |
| 397175 | 10/1990 | (EP) . |
| 0 407 217 A1 | 1/1991 | (EP) . |
| 418 845 A1 | 3/1991 | (EP) . |
| 0 560 407 A1 | 9/1993 | (EP) . |
| 0 566 175 A2 | 10/1993 | (EP) . |
| 300 278 | 7/1998 | (EP) . |
| 2 000 170 | 1/1979 | (GB) . |
| 48-091058 | 11/1973 | (JP) . |
| 48-09161 | 11/1973 | (JP) . |
| 50-121261 | 9/1975 | (JP) . |
| 63-68581 | of 1988 | (JP) . |
| 4 279 672 | 10/1992 | (JP) . |
| 4-327583 | 11/1992 | (JP) . |
| WO 91/16055 | 10/1991 | (WO) . |
| WO 91/19708 | 12/1991 | (WO) . |
| WO 94/15932 | 1/1993 | (WO) . |
| WO 94/15932 | 7/1994 | (WO) . |
| WO 95/00501 | 1/1995 | (WO) . |
| WO 95/05376 | 2/1995 | (WO) . |
| WO 95/18799 | 7/1995 | (WO) . |

OTHER PUBLICATIONS

Lombardino, Nonsteroidal Antiinflammatory Drugs, PP 114–130 (1985).
Doyama, et al., J. Chem. Soc. Chem. Commun., PP 649–650 (1987).
Joh, et al—Organometallics, vol. 10, pp. 2493–2498 (1991).
Vijayaraghavan, et al—Indian Journal of Chemistry, vol. 25B, pp 760–761 (1986).

(List continued on next page.)

*Primary Examiner*—Bernard Dentz
(74) *Attorney, Agent, or Firm*—Curtis C. Panzer; David L. Rose

(57) ABSTRACT

The invention encompasses the novel compound of Formula I useful in the treatment of cyclooxygenase-2 mediated diseases.

The invention also encompasses certain pharmaceutical compositions for treatment of cyclooxygenase-2 mediated diseases comprising compounds of Formula I.

10 Claims, No Drawings

OTHER PUBLICATIONS

Ford, et al—Preparation Of 2(5H)–Furanones, PP 173–177 (1967).
Translation of paragraphs 2–8 of JP 04–327583A (1992).
Toda, et al—J. Chem. Soc. Chem. Comm., vol. 18, No. 1234–1235 (1984).
Ahmed, et al—Egypt J. Chem., vol. 33, No. 3, pp. 291–295 (1990).
Ahmed, et al—Rev. Roum Chim., vol. 38, No. 1, pp. 79–82 (1993).
Tetrahedron Letters, vol. 29, No. 28, pp. 3483–3486 (1988).
Chem. and Pharm. Bull., vol. 29, No. 3, PP 635–645 (1981).
Journal of the Chem. Soc. Chem. Comm., No. 8, pp. 656–658 (1992).
Cremlyn, et al—CA 105: 133845 (1986).
Myers, M., et al—J. Res. Discl., vol. 253, pp. 223–224, (1985).
Wilkerson, W.—J. Res. Discl., vol. 266, pp. 323–324 (1986).
Wilkerson, W., et al—J. Res. Discl., vol. 253, pp. 220–222 (1985).
J. Org. Chem., vol. 60, No. 17, pp. 5419–5424 (1995).
Tetrahedron, vol. 25, No. 44, pp. 5043–5046 (1984).
Tetrahedron, vol. 38, No. 11, pp. 1609–1613 (1982).
J. Heterocycle Chem., vol. 11, No. 5, pp. 797–802 (1974).
Chem. Ber., vol. 123, No. 7, pp. 1553–1562 (1990).
U.S. application No. 08/109,751, Berryman et al.
Dikshit, et al., Indian Journal of Chemistry, vol. 29B, Oct. 1990, pp. 954–960.
O. Dann. et al. 11 Mitt.: Pharmazie 23, 69, pp. 135–145 (1968).
M. Gindy, et al., J. Indian Chem. Soc., vol. LIII, pp. 490–495 (May 1976).
J. Nakayama, et al., Tetrahedron Letters, vol. 30, No. 7, pp. 847–850 (1989).
J. Nakayama, et al., Tetrahedron Letters, vol. 23, No. 8, pp. 1907–1910 (1985).
D.J. Chadwick, et al., Preparation of Thiophen Esters by the Hinsberg Reaction. pp. 2079–2081 (1972).
O'Banion. et al., Proc. Natl. Acad. Sci, USA, vol. 89, pp. 4888–4892 (1992).
Lombardino, et al., Arzneim–Forsch. (Drug Res.), vol. 25, NR. 10, pp. 1629–1635 (1975).
Chem. Abstracts vol. 67, No. 17, Ab. No. 82088e (Oct. 23, 1967).
Chem. Abstracts vol. 55, No. 4, Ab. No. 3553g (Feb. 20, 1961) Arch. Pharm., vol. 293, pp. 187–194 (1960).
Chem. Abstracts, vol. 55, No. 1, Ab. No. 502g (Jan. 9, 1961)–Farmaco Ed. Sci., vol.15, Pavia It., pp. 442–450 (1960).
Chemische Berichet, vol. 116, pp. 3112–3124 (1983).
Chemical Abstracts, vol. 113, No. 21, ab. No. 184393m (1990) Gans, et al., J. Pharmacol. Exp. Ther., vol. 254, No. 1, pp. 180–187 (1990).
Ahluwalia, et al., Synth. commun., vol. 19, No. 3–4, pp. 619–626 (1989).

* cited by examiner

3-PHENYL-4-(4(METHYLSULFONYL) PHENYL)-2-(5H)-FURANONE AS A COX-2 INHIBITOR

CROSS REFERENCE TO RELATED APPLICATIONS

This is a continuation application of U.S. Ser. No. 08/672,562, filed on Jun. 28, 1996, which is a continuation application of U.S. Ser. No. 08/435,060, filed May 8, 1995 now abandoned, which is Divisional application of U.S. Ser. No. 08/179,467, filed Jan. 10, 1994 (now U.S. Pat. No. 5,474,995), which is a continuation-in-part of U.S. Ser. No. 08/082,196, filed Jun. 24, 1993 now abandoned.

BACKGROUND OF THE INVENTION

This invention relates to compounds and pharmaceutical compositions for the treatment of cyclooxygenase mediated diseases and methods of treatment thereof.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

SUMMARY OF THE INVENTION

The invention encompasses novel compounds of Formula I useful in the treatment of cyclooxygenase-2 mediated diseases.

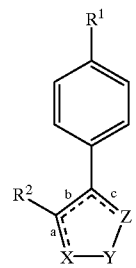

The invention also encompasses certain pharmaceutical compositions and methods for treatment of cyclooxygenase-2 mediated diseases comprising the use of compounds of Formula I.

DETAILED DESCRIPTION OF THE INVENTION

The invention encompasses the novel compound of Formula I useful in the treatment of cyclooxygenase-2 mediated diseases

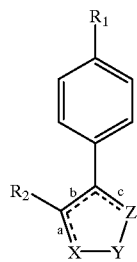

I or pharmaceutically acceptable salts thereof wherein:
X—Y—Z-is selected from the group consisting of:
(a) —$CH_2CH_2CH_2$—,
(b) —$C(O)CH_2CH_2$—,
(c) —$CH_2CH_2C(O)$—,
(d) —$CR^5(R^{5'})$—O—C(O)—,
(e) —C(O)—O—$CR^5(R^{5'})$—,
(f) —$CH_2$—$NR^3$—$CH_2$—,
(g) —$CR^5(R^{5'})$—$NR^3$—C(O)—,
(h) —$CR^4$=$CR^{4'}$—S—,
(i) —S—$CR^4$=$CR^{4'}$—,
(j) —S—N=CH—,
(k) —CH=N—S—,
(l) —N=$CR^4$—O—,
(m) —O—CR4=N—
(n) —N=$CR^4$—NH—;
(o) —N=$CR^4$—S—, and
(p) —S—$CR^4$=N—;
(q) —C(O)—$NR^3$—$CR^5(R^{5'})$—;
(r) —$R^3$N—CH=CH— provided $R^1$ is not —$S(O)_2$Me
(s) —CH=CH—$NR^3$— provided $R^1$ is not —$S(O)_2$Me when side b is a double bond, and sides a an c are single bonds; and
X—Y—Z-is selected from the group consisting of:
(a) =CH—O—CH=, and
(b) =CH—$NR^3$—CH=,
(c) =N—S—CH=,
(d) =CH—S—N=,
(e) =N—O—CH=, (f) =CH—O—N=,
(g) =N—S—N=,
(h) =N—O—N=,
when sides a and c are double bonds and side b is a single bond;

$R^1$ is selected from the group consisting of
(a) $S(O)_2CH_3$,
(b) $S(O)_2NH_2$,
(c) $S(O)_2NHC(O)CF_3$,
(d) $S(O)(NH)CH_3$,
(e) $S(O)(NH)NH_2$,
(f) $S(O)(NH)NHC(O)CF_3$,
(g) $P(O)(CH_3)OH$, and
(h) $P(O)(CH_3)NH_2$, $R^2$ is selected from the group consisting of
(a) $C_{1-6}$alkyl,
(b) $C_3$, $C_4$, $C_5$, $C_6$, and $C_7$, cycloalkyl,
(c) mono-, di- or tri-substituted phenyl or naphthyl wherein the substituent is selected from the group consisting of
(1) hydrogen,
(2) halo,
(3) $C_{1-6}$alkoxy,
(4) $C_{1-6}$alkylthio,
(5) CN,
(6) $CF_3$,
(7) $C_{1-6}$alkyl,
(8) $N_3$,
(9) —$CO_2H$,
(10) —$CO_2$—$C_{1-4}$alkyl,
(11) —$C(R^5)(R^6)$—OH,
(12) —$C(R^5)(R^6)$—O—$C_{1-4}$alkyl, and
(13) —$C_{1-6}$alkyl-$CO_2$—$R^5$;
(d) mono-, di- or tri-substituted heteroaryl wherein the heteroaryl is a monocyclic aromatic ring of 5 atoms, said ring having one hetero atom which is S, O, or N, and optionally 1, 2, or 3 additionally N atoms; or the heteroaryl is a monocyclic ring of 6 atoms, said ring having one hetero atom which is N, and optionally 1, 2, 3, or 4 additional N atoms; said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH, and
(10) —$C(R^5)(R^6)$—O—$C_{1-4}$alkyl;
(e) benzoheteroaryl which includes the benzo fused analogs of (d);

$R^3$ is selected from the group consisting of
(a) hydrogen,
(b) $CF_3$,
(c) CN,
(d) $C_{1-6}$alkyl,
(e) hydroxy$C_{1-6}$alkyl,
(f) —C(O)—$C_{1-6}$alkyl,
(g) optionally substituted
(1) —$C_{1-5}$ alkyl-Q,
(2) —$C_{1-3}$alkyl-O—$C_{1-3}$alkyl-Q,
(3) —$C_{1-3}$alkyl-S—$C_{1-3}$alkyl-Q,
(4) —$C_{1-5}$ alkyl-O—Q, or
(5) —$C_{1-5}$ alkyl-S—Q,
wherein the substituent resides on the alkyl and the substituent is $C_{1-3}$alkyl;
(h) —Q $R^4$ and $R^{4'}$ are each independently selected from the group consisting of
(a) hydrogen,
(b) $CF_3$,
(c) CN,
(d) $C_{1-6}$alkyl,
(e) —Q,
(f) —O—Q;
(g) —S—Q, and
(h) optionally substituted
(1) —$C_{1-5}$ alkyl-Q,
(2) —O—$C_{1-5}$ alkyl-Q,
(3) —S—$C_{1-5}$ alkyl-Q,
(4) —$C_{1-3}$alkyl-O—$C_{1-3}$alkyl-Q,
(5) —$C_{1-3}$alkyl-S—$C_{1-3}$alkyl-Q,
(6) —$C_{1-5}$ alkyl-O—Q,
(7) —$C_{1-5}$ alkyl-S—Q,
wherein the substituent resides on the alkyl and the substituent is $C_{1-3}$alkyl, and $R^5$, $R^{5'}$, $R^6$, $R^7$ and $R^8$ are each independently selected from the group consisting of
(a) hydrogen,
(b) $C_{1-6}$alkyl,
or $R^5$ and $R^6$ or $R^7$ and $R^8$ together with the carbon to which they are attached form a saturated monocyclic carbon ring of 3, 4, 5, 6 or 7 atoms;

Q is $CO_2H$, $CO_2$—$C_{1-4}$alkyl, tetrazolyl-5-yl, $C(R^7)(R^8)$ (OH), or
$C(R^7)(R^8)(O$—$C_{1-4}$alkyl);
provided that when X—Y—Z is —S—$CR^4$=$CR^{4'}$, then $R^4$ and $R^{4'}$ are other than $CF_3$.

One Class within this embodiment are the compounds of formula I

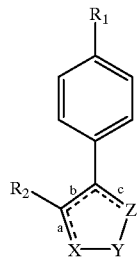

I or pharmacetically acceptable salts thereof wherein:
X—Y—Z— is selected from the group consisting of
—C(O)—O—$CR^5(R^{5'})$— when side b is a double bond, and sides a and c are single bonds; and $R^1$ is selected from the group consisting of
(a) $S(O)_2CH_3$,
(b) $S(O)_2NH_2$, $R^2$ is selected from the group consisting of
(a) $C_{1-6}$alkyl,
(b) $C_3$, $C_4$, $C_5$, $C_6$, and $C_7$, cycloalkyl,
(c) heteroaryl
(d) benzoheteroaryl
(e) mono- or di-substituted phenyl wherein the substituent is selected from the group consisting of
(1) hydrogen,
(2) halo,
(3) $C_{1-6}$alkoxy,
(4) $C_{1-6}$alkylthio,
(5) CN, (6) $CF_3$,
(7) $C_{1-6}$alkyl,
(8) $N_3$,
(9) —$CO_2H$,
(10) —$CO_2$—$C_{1-4}$alkyl,
(11) —$C(R^5)(R^6)$—OH,
(12) —$C(R^5)(R^6)$—O—$C_{1-4}$alkyl, and
(13) —$C_{1-6}$alkyl-$CO_2$—$R^5$;

$R^5$, $R^{5'}$ and $R^6$ are each independently selected from the group consisting of
(a) hydrogen,
(b) $C_{1-6}$alkyl,
or $R^5$ and $R^6$ together with the carbon to which they are attached form a saturated monocyclic carbon ring of 3, 4, 5, 6 or 7 atoms.

For purposes of this specification alkyl is defined to include linear, branched, and cyclic structures, with $C_{1-6}$alkyl including including methyl, ethyl, propyl, 2-propyl, s- and t-butyl, butyl, pentyl, hexyl, 1,1-dimethylethyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$alkylthio is intended to include alkylthio groups of from 1 to 6 carbon atoms of a straight, branched or cyclic configuration. Examples of lower alkylthio groups include methylthio, propylthio, isopropylthio, cycloheptylthio, etc. By way of illustration, the propylthio group signifies —$SCH_2CH_2CH_3$.

Heteroaryl includes furan, thiophene, pyrrole, isoxazole, isothiazole, pyrazole, oxazole, thiazole, imidazole, 1,2,3-oxadiazole, 1,2,3-thiadiazole, 1,2,3-triazole, 1,3,4-oxadiazole, 1,3,4-thiadiazole, 1,3,4-triazole, 1,2,5-oxadiazole, 1,2,5-thiadiazole, pyridine, pyridazine, pyrimidine, pyrazine, 1,2,4-triazine, 1,3,5-triazine, 1,2,4,5-tetrazine, and the like.

Benzoheteroaryl includes the above heteroaryl rings to which it is possible to fuse a benzene ring.

Exemplifying the invention are:

(a) 3-(4-(Aminosulfonyl)phenyl)-2-(4-fluorophenyl)-5-(2-hydroxy-2-propyl)thiophene,
(b) 3-(4-(Aminosulfonyl)phenyl)-2-(4-fluorophenyl)thiophene,
(c) 3-(4-(Aminosulfonyl)phenyl)-2-(4-fluorophenyl)-5-(2-propyl)thiophene,
(d) 3-(4-(Aminosulfonyl)phenyl)-2-cyclohexylthiophene,
(e) 5-(4-Carboxyphenyl)-4-(4-(methylsulfonyl)phenyl)thiophene-2-carboxylic acid,
(f) 4-(4-Fluorophenyl)-2-methyl-5-(4-(methylsulfonyl)phenyl)thiazole,
(g) 2-(4-Fluorophenyl)-3-(4-(methylsulfonyl)phenyl)-2-cyclopenten-1-one
(h) 4-(4-(Methylsulfonyl)phenyl)-5-(4-fluorophenyl)-isothiazole,
(i) 3-(4-Fluorophenyl)-4-(4-(methylsulfonyl)phenyl)-2-(5H)-furanone,
(j) 3-(4-Fluorophenyl)-4-(4-(aminosulfonyl)phenyl)-2-(5H)-furanone,
(k) 3-(4-Fluorophenyl)-4-(4-(methylsulfonyl)phenyl)furan,
(l) 5,5-Dimethyl-3-(4-fluorophenyl)-4-(4-methylsulfonyl)phenyl)-2-(5H)-furanone,
(m) 2-(4-(Aminosulfonyl)phenyl)-3-(4-fluorophenyl)thiophene, and
(n) 3-(4-(Trifluoroacetylaminosulfonyl)phenyl)-2-(4-fluorophenyl)thiophene,
(o) 3-(3-Fluorophenyl)-4-(4-(methylsulfonyl)phenyl)-2-(5H)-furanone,
(p) 5,5-Dimethyl-3-(3-fluorophenyl)-4-(4-methylsulfonyl)phenyl)-2-(5H)-furanone,
(q) 5,5-Dimethyl-3-(3-chlorophenyl)-4-(4-methylsulfonyl)phenyl)-2-(5H)-furanone,
(r) 3-(3,4-Difluorophenyl)-4-(4-(methylsulfonyl)phenyl)-2-(5H)-furanone,
(s) 3-(3,4-Dichlorophenyl)-4-(4-(methylsulfonyl)phenyl)-2-(5H)-furanone,
(t) 5,5-Dimethyl-3-(3,4-difluorophenyl)-4-(4-methylsulfonyl)phenyl)-2-(5H)-furanone,
(u) 5,5-Dimethyl-3-(3,4-dichlorophenyl)-4-(4-methylsulfonyl)phenyl)-2-(5H)-furanone,
(v) 5,5-Dimethyl-3-(4-chlorophenyl)-4-(4-methylsulfonyl)phenyl)-2-(5H)-furanone,
(w) 3-(2-Naphyhyl)-4-(4-(methylsulfonyl)phenyl)-2-(5H)-furanone,
(x) 5,5-Dimethyl-3-(2-naphyhyl)-4-(4-(methylsulfonyl)phenyl)-2-(5H)-furanone,
(y) 3-phenyl-4-(4-(methylsulfonyl)phenyl)-2-(5H)-furanone.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of compound of formula I as described above.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of compound of formula I as described above.

In a third embodiment, the invention encompasses a method of inhibiting cyclooxygenase and treating cyclooxygenase mediated diseases, advantageously treated by an active agent that selectively inhibits COX-2 in preference to COX-1 as disclosed herein comprising: administration to a patient in need of such treatment of a non-toxic therapeutically effective amount of a compound of Formula I as disclosed herein.

For purposes of this specification a compound is said to selectively inhibit COX-2 in preference to COX-1 if the ratio of the IC50 concentration for COX-1 inhibition to COX-2 inhibition is 100 or greater.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occuring substituted amines, cyclic amines, and basic ion exchange resins, such as arginine, betaine, caffeine, choline, N,N_-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of formula I may also be useful for the treatment of dementia including pre-senile and senile dementia, and in particular, dementia associated with Alzheimer Disease (ie Alzheimer's dementia).

Compounds of formula I will also inhibit prostanoid-induced smooth muscle contraction by preventing the synthesis of contractile prostanoids and hence may be of use in the treatment of dysmenorrhea, premature labor and asthma.

By virtue of its high cyclooxygenase-2 (COX-2) activity and/or its selectivity for cyclooxygenase-2 over cyclooxygenase-1 (COX-1) as defined above, compounds of formula I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (eg impaired renal function); those prior to surgery or taking anticoagulants; and those susceptable to NSAID induced asthma.

Similarly, compounds of formula I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

Compounds of the present invention are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of formula I. The IC50 values represent the concentration of inhibitor required to return $PGE_2$ synthesis to 50% of that obtained as compared to the uninhibited control. Illustrating this aspect, we have found that the Compounds of the Examples are more than 100 times more effective in inhibiting COX-2 than they are at inhibiting COX-1. In addition they all have a COX-2 IC50 of 1 nM to 1 $\mu$M. By way of comparison, Ibuprofen has an IC50 for COX-2 of 1 $\mu$M, and Indomethacin has an IC50 for COX-2 of approximately 100 nM. For the treatment of any of these cyclooxygenase mediated diseases, compounds of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of Synthesis

The compounds of the present invention can be prepared according to the following methods.

Method A

The β-chlorovinylaldehyde III can be obtained from the ketone II and the Vilsmeier reagent (DMF-POCl$_3$) using the general method described by Weissenfels (Z. Chem. 1966, 6, 471). The thiophene compound IV is obtained from III using the general method described by Weissenfels (Z. Chem., 1973, 13, 57). The thiol compound V can be obtained after oxidation of compound IV ($R^a$=—SMe) with one equivalent of m-CPBA followed by treatment of the resulting sulfoxide with TFAA at reflux. The sulfonamide group (VI) can then be formed by the method of Kharash (J. Amer. Chem. Soc. 1951, 73, 3240). The hydrolysis of compound VI and decarboxylation with Cu bronze in quinoline provides compound VII. Compound VII ($R^4$=H) can be treated with halogenating agent such as bromine in acetic acid to allow the preparation of the 5-bromothiophene (VII, $R^4$=Br). When it is desired to have a nitrile group at C-5, this can be accomplished from VI via amide formation using the Weinreb methodology (Tetrahedron Letters, 1977, 4171) followed by dehydration with TFAA. The $CF_3$ group can be introduced at C-5 of VII via the method of Girard (J. Org. Chem. 1983, 48, 3220).

The introduction of an alkyl group at C-5 can be achieved via a Friedel-Crafts reaction on VII ($R^4$=H) and an acyl chloride, Cl—CO- lower alkyl and a catalyst such as $TiCl_4$, followed by reduction. For $R^4$=Me, this can be achieved from the ester ($R^4$=$CO_2Me$) via a DIBAL-H reduction followed by deoxygenation using the method of Lau (J. Org. Chem. 1986, 51, 3038). Tertiary alcohols ($R^4$=—C($CH_3$)$_2$OH) can be obtained from VI and MeMgBr. These tertiary alcohols can also be deoxygenated using the method of Lau. Similarly, the thiophene IX can be prepared from ketone VIII.

Method A

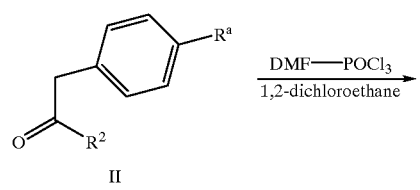

II $R^a$ = —SMe or —$SO_2Me$

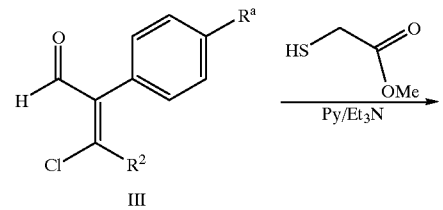

III

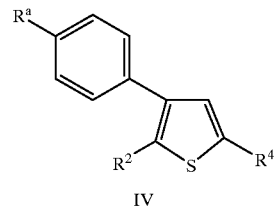

IV ($R^4$ = —$CO_2Me$)

$R^a$ = $SO_2Me$
$R^2$ = $PhCO_2H$
$R^4$ = $CO_2H$ when $R^a$ is SMe 1. m-CPBA/$CH_2Cl_2$
2. TFAA

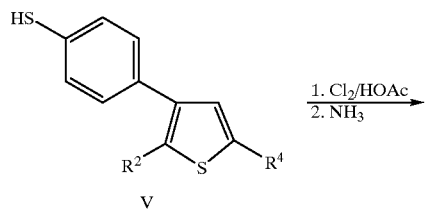

V ($R^4$ = -$CO_2Me$)

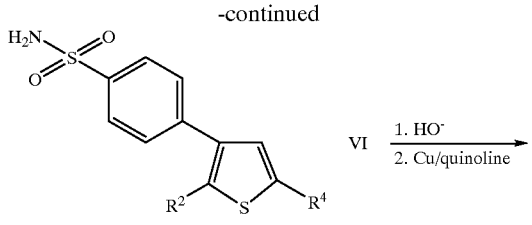

VI ($R^4$ = $CO_2Me$)

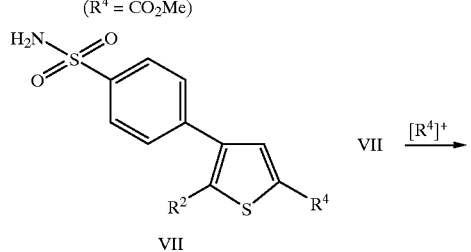

VII ($R^4$ = H)

$R^4$ = Br
VII $R^4$ = $C_1$-$C_6$ alkyl  VI $\xrightarrow{\text{1. amidation} \atop \text{2. TFAA}}$ VI $R^4$ = CN
$R^4$ = $CF_3$ VI $\xrightarrow{MeMgBr}$ VI
($R^4$ = —C($CH_3$)$_2$OH)

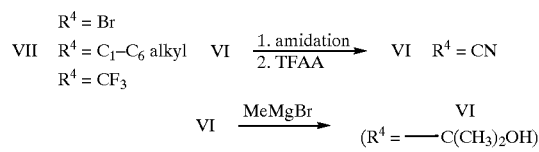

VIII

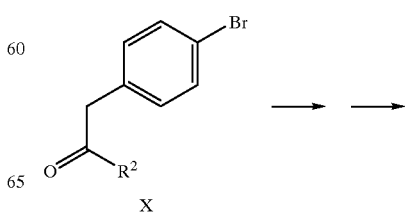

IX

Method B

Ketone X can be converted to the thiophene compound XI using general methods already described in Method A. The thiophene XII can be prepared by metallation of XI with n-BuLi, quenching with methyl phosphonic dichloride and addition of water or ammonia (X'=OH or $NH_2$). Similarly, the other regioisomer XIV can be prepared from ketone XIII.

Method B

X

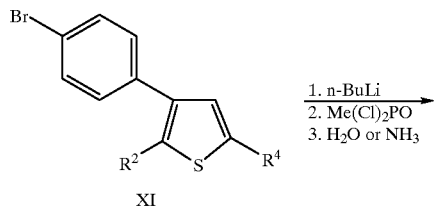

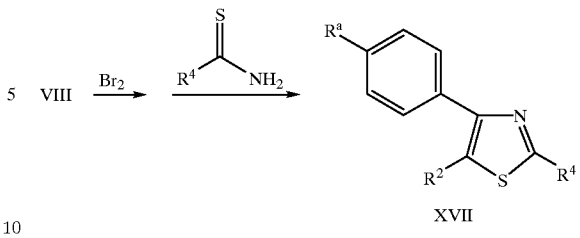

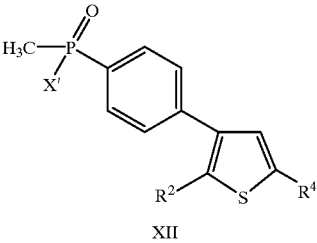

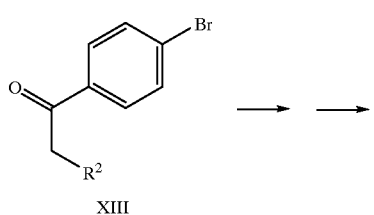

Method C

Bromination of ketone II gives the α-bromoketone XV which is then converted to the thiazole XVI after treatment with a thioamide. Similarly, ketone VIII can be converted to thiazole XVII.

Method C

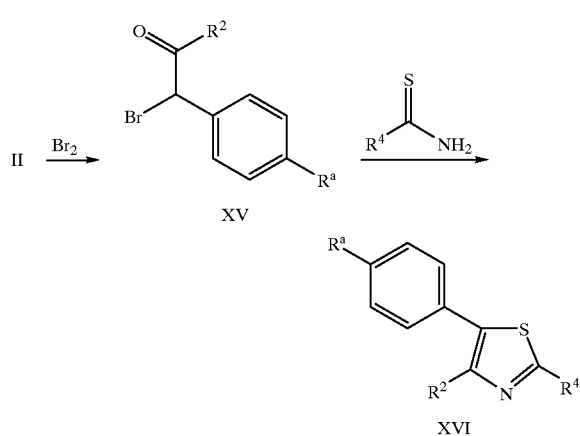

Method D

Ketone XV can be converted to the imidazole compound XVIII after treatment with formamide using the preparation of Brederick et al, Chem. Ber. 1953, p. 88.

Method D

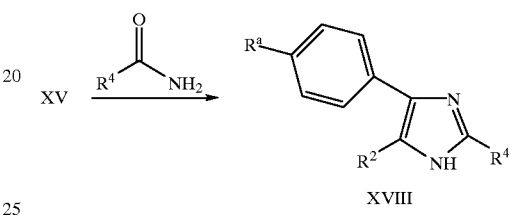

Method E

Pyrole compound XX can be obtained from diketone XIX using the general procedures of Friedman et al, J. Org. Chem. 1965, 30, p. 854, K. Dimroth et al, Ber. 1956, 56, 2602, K. Dimroth et al, Ann. 1961, 634, 102. The free NH of the pyrole can be acylated with Cl—CO-lower alkyl in the presence of a base such as $Et_3N$. Also alkylated products can be prepared using alkyl halides as reagents with a base such as NaH.

Method E

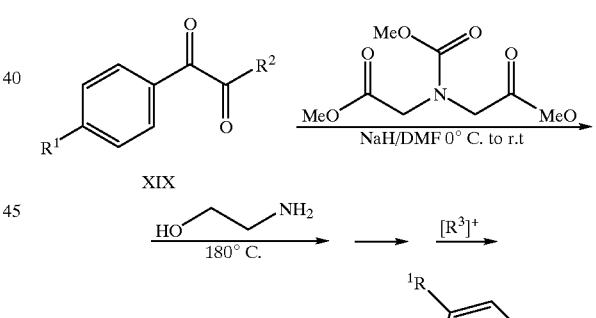

Method F

The compounds of type XXV can be prepared from readily available 4-substituted phenylacetyl chlorides XXIa. Reaction of di(3-butenyl)cadmium with a 4-substituted phenylacetyl chloride provides ketone XXI. Ozonolysis of XXI affords keto aldehyde XXIb which is cyclized by base to give cyclopentenone XXII. Addition of arylmagnesium bromide or aryllithium to XXII gives allylic alcohol XXIV.

Oxidation of XXIV with pyridinium chlorochromate affords the desired 2,3-disubstituted cyclopentenone XXV. For preparation of compound XXV ($R^1=SO_2Me$), 4-methylthiophenyllithium is used followed by oxidation with the magesium salt of monoperoxyphthalic acid (MMPP) or m-chloroperoxybenzoic acid (mCPBA) to introduce the required methylsulfonyl group in XXV.

Method F

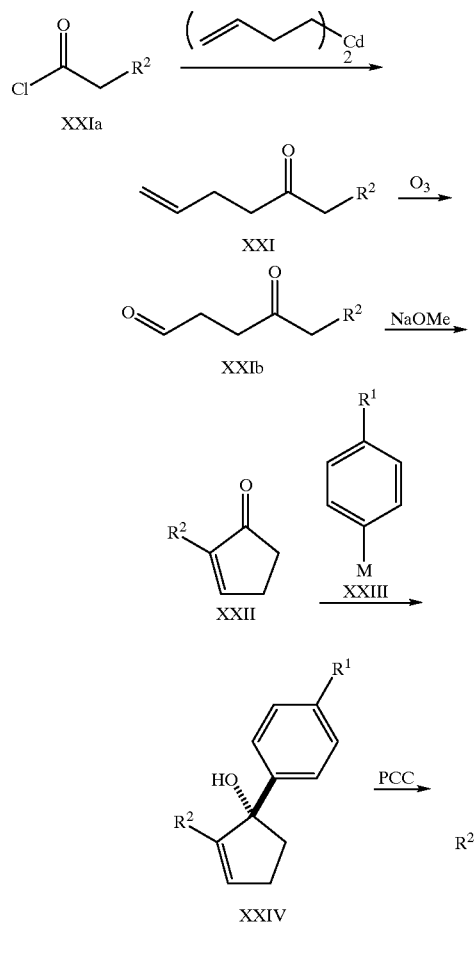

Method G

The sequence of Method G is the same as in Method F except $R^1$ containing acid chloride is used as starting material. $R^2$ is introduced at a later stage via a carbonyl addition reaction, followed by PCC oxidation.

Method G

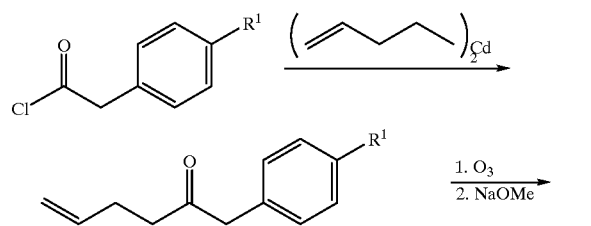

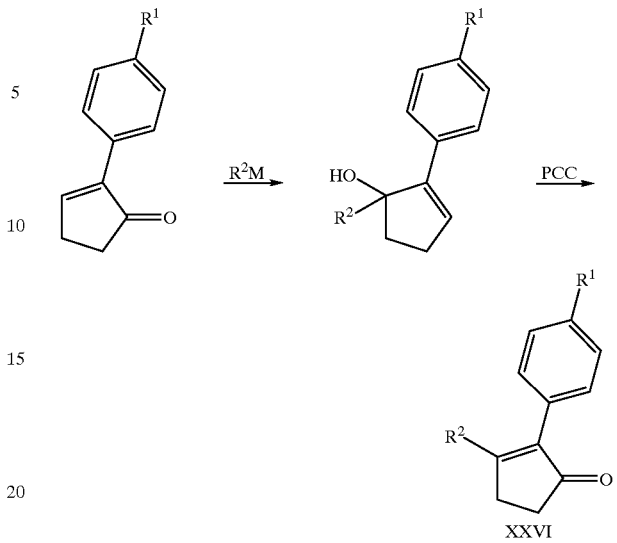

Method H

The 4,5-disubstituted isothiazoles and isothiazol-3(2H)-one-1,1-dioxides can be prepared by the general method described by B. Schulze et al, Helvetica Chimica Acta, 1991, 74, 1059. Thus, aldehyde III ($R^a=SO_2Me$) or XXVII is treated with excess $NH_4SCN$ in refluxing acetone to provide the corresponding 4,5-disubstituted isothiazoles XXX and XXVIII, oxidation of which with hydrogen peroxide yields XXXI and XXIX.

Method H

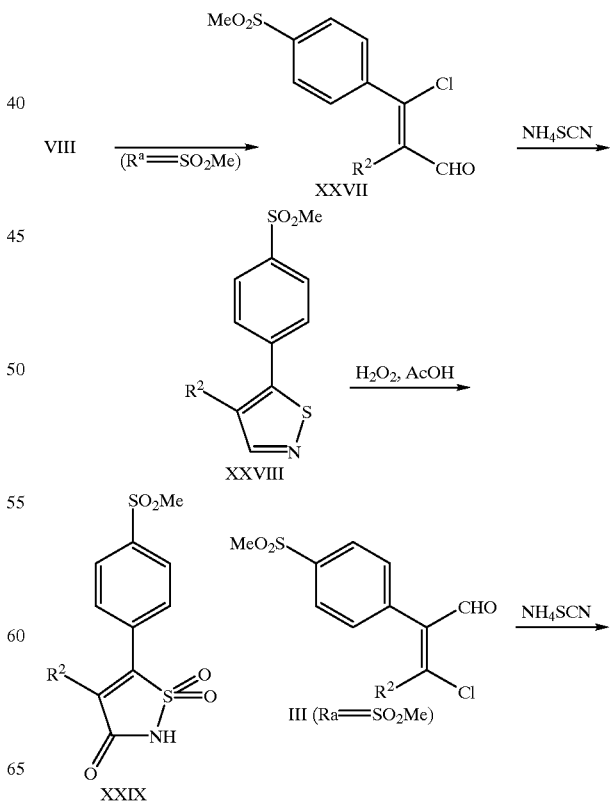

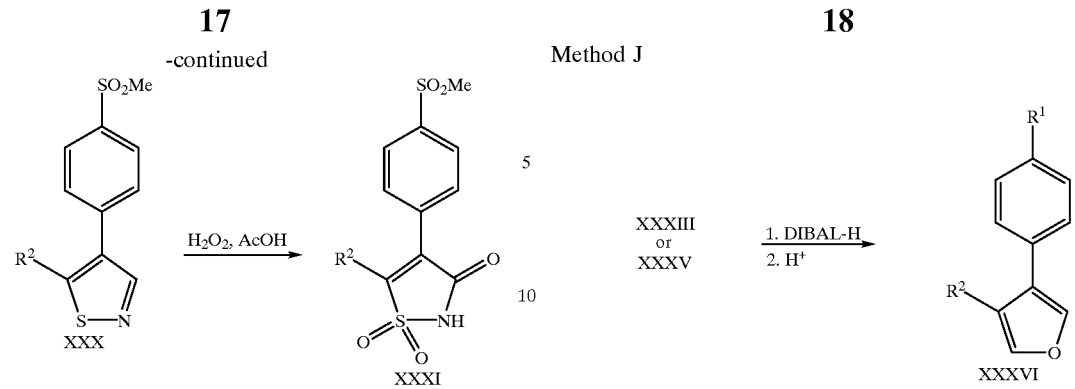

Method I

An appropriately substituted aryl bromomethyl ketone is reacted with an appropriately substituted aryl acetic acid in a solvent such as acetonitrile in the presence of a base such as triethylamine and then treated with 1,8-diazabicyclo[5.4.0]undec-7-ene (DBU) to afford either the lactone XXXIII or XXXV.

Method I

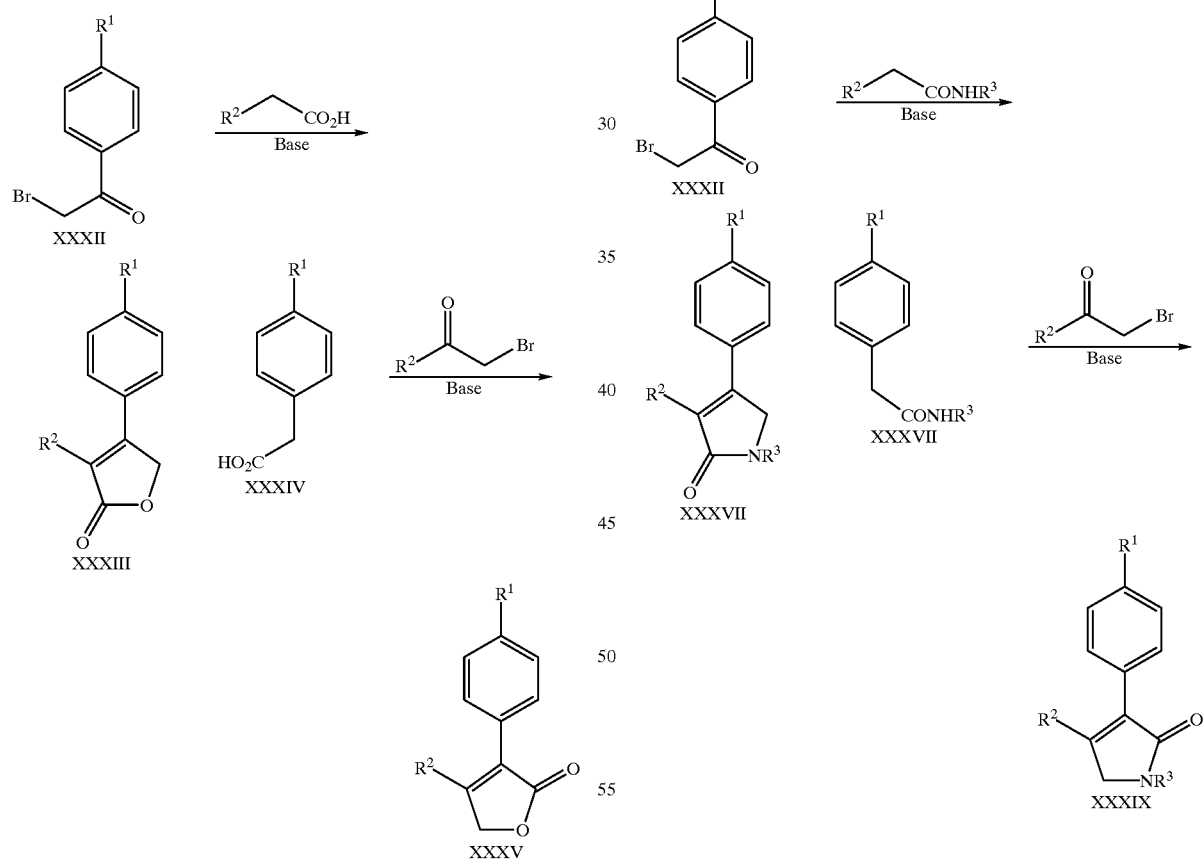

(R² is a mono- or disubstituted phenyl or a mono- or disubstituted heteroaryl)

Method J

Either of the lactones XXXIII or XXXV in a solvent such as THF is reacted with a reducing agent such as diisobutyl aluminium hydride or lithium borohydride at −78° C., to yield the furan XXXVI.

Method J

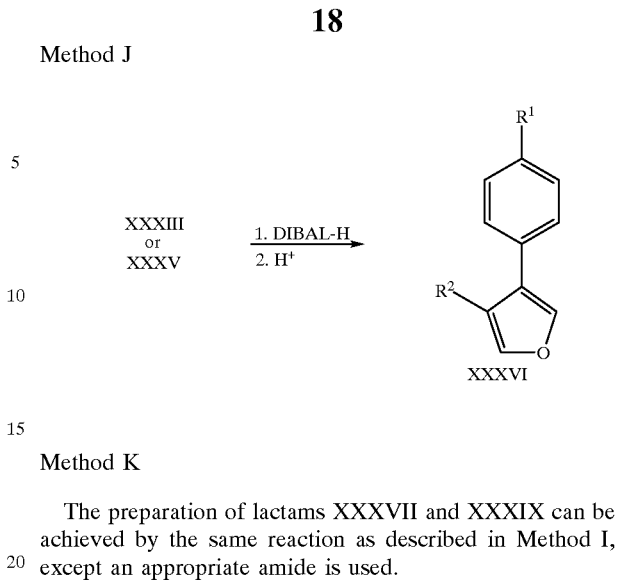

Method K

The preparation of lactams XXXVII and XXXIX can be achieved by the same reaction as described in Method I, except an appropriate amide is used.

Method K

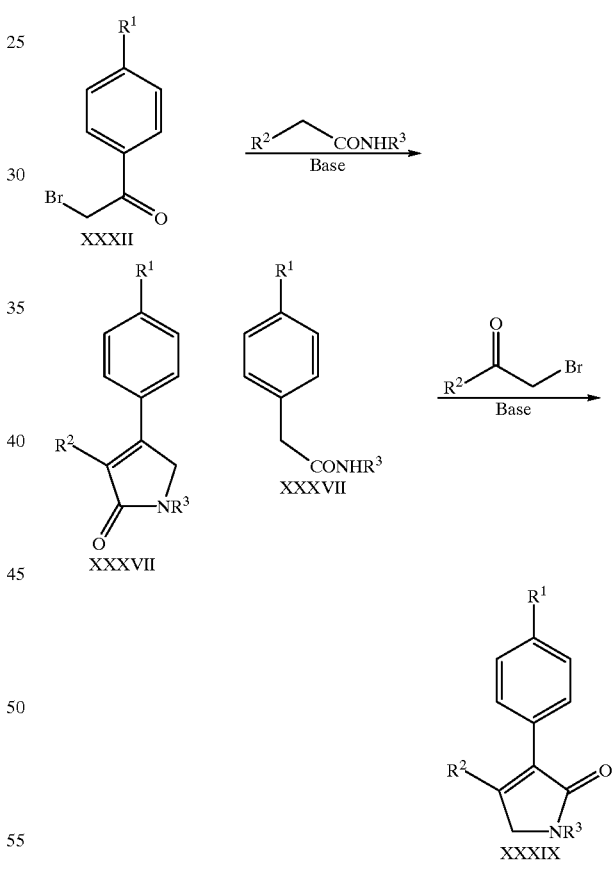

Method L

Methyl 2-hydroxy isobutyrate is silylated with TMSCl to give the TMS ether XXXXI, which is treated with 4-methylthiophenyllithium to provide ketone XXXXII. Desilylation followed by acylation yields keto-ester XXXXIV, which can be cyclized to lactone XXXXV by base catalysis. Oxidation of XXXXV with MMPP or mCPBA affords the desired product XXXXVI.

Method L

Method M

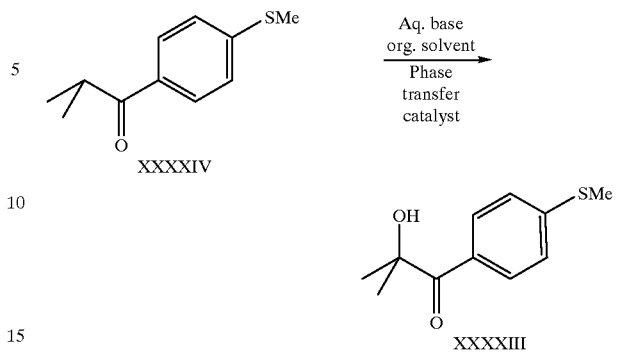

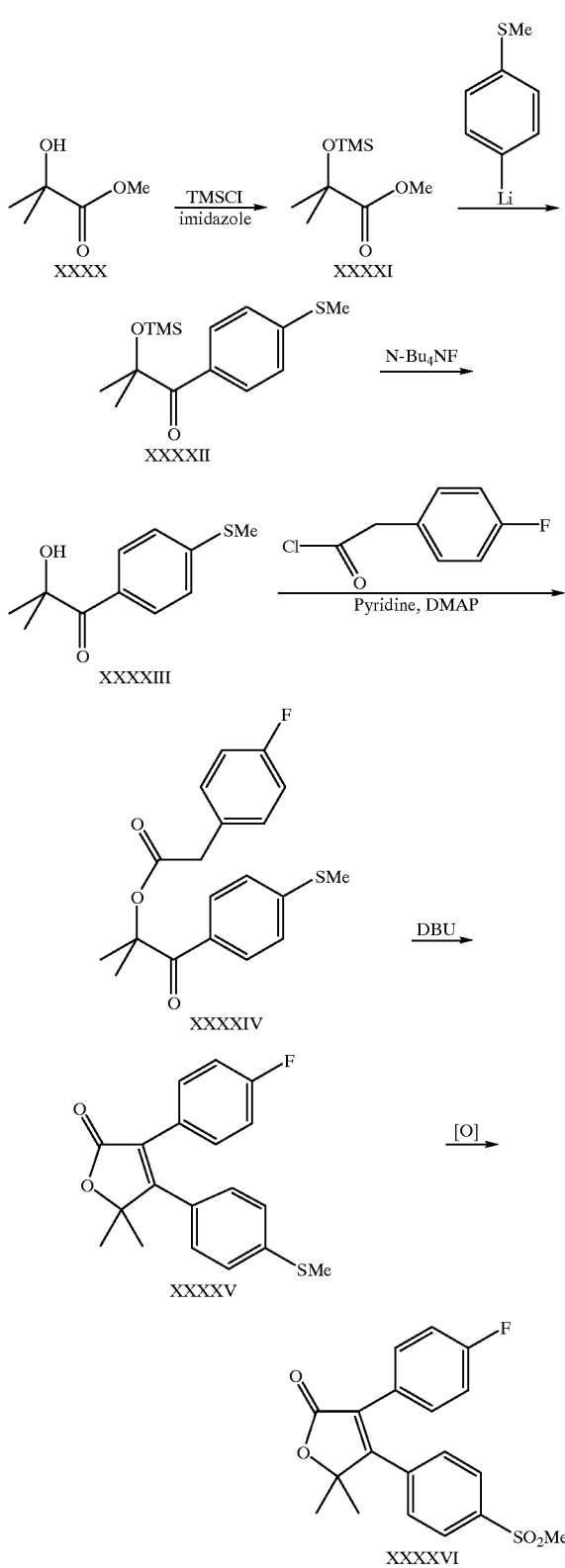

An alternative preparation of the hydroxy ketone XXXXIII is the oxidation of the known (J. Org. Chem. 1991 56, 5955–8; Sulfur Lett. 1991, 12, 123–32) ketone XXXXIV. A mixture of XXXXIV, aquous base, such as NaOH, organic solvents such as carbon tetrachloride/toluene and a phase transfer catalyst such as ALIQUAT 336 is stirred in air at room temperature to provide XXXXIII. Compound XXXXIII is also described in U.S. Pat. No. 4,321,118 and Org. Coat. 1986, 6, 175–95.

Representative Compounds

Tables I and II illustrate compounds of formula I.

TABLE I

| | Example | Method |
|---|---|---|
| ![structure] | 1 | A |
| ![structure] | 2 | A |
| ![structure] | 3 | A |

TABLE I-continued

| Structure | Example | Method |
|---|---|---|
| 3-(4-sulfamoylphenyl)-2-cyclohexylthiophene | 4 | A |
| 4-(4-methylsulfonylphenyl)-5-(4-carboxyphenyl)thiophene-2-carboxylic acid | 5 | A |
| 4-(4-fluorophenyl)-2-methyl-5-(4-methylsulfonylphenyl)thiazole | 6 | C |
| 2-(4-fluorophenyl)-3-(4-methylsulfonylphenyl)cyclopent-2-enone | 7 | F |
| 5-(4-fluorophenyl)-4-(4-methylsulfonylphenyl)isothiazole | 8 | H |
| 3-(4-fluorophenyl)-4-(4-methylsulfonylphenyl)-2(5H)-furanone | 9 | I |
| 3-(4-fluorophenyl)-4-(4-sulfamoylphenyl)-2(5H)-furanone | 10 | I |
| 3-(4-fluorophenyl)-4-(4-methylsulfonylphenyl)furan | 11 | J |
| 3-(4-fluorophenyl)-4-(4-methylsulfonylphenyl)-5,5-dimethyl-2(5H)-furanone | 12 | L |
| 3-(4-fluorophenyl)-2-(4-sulfamoylphenyl)thiophene | 13 | A |

TABLE I-continued

| | Example | Method |
|---|---|---|
| (3-(4-SO2NHC(O)CF3-phenyl)-2-(4-fluorophenyl)thiophene) | 14 | A |
| (3-(2,4-difluorophenyl)-4-(4-methylsulfonylphenyl)-2(5H)-furanone) | 15 | I |
| (3-(3,4-difluorophenyl)-4-(4-methylsulfonylphenyl)-2(5H)-furanone) | 16 | I |
| (3-(2,6-difluorophenyl)-4-(4-methylsulfonylphenyl)-2(5H)-furanone) | 17 | I |
| (3-(2,5-difluorophenyl)-4-(4-methylsulfonylphenyl)-2(5H)-furanone) | 18 | I |
| (3-(3,5-difluorophenyl)-4-(4-methylsulfonylphenyl)-2(5H)-furanone) | 19 | I |
| (3-(4-bromophenyl)-4-(4-methylsulfonylphenyl)-2(5H)-furanone) | 20 | I |
| (3-(4-chlorophenyl)-4-(4-methylsulfonylphenyl)-2(5H)-furanone) | 21 | I |
| (3-(4-methoxyphenyl)-4-(4-methylsulfonylphenyl)-2(5H)-furanone) | 22 | I |
| (3-phenyl-4-(4-methylsulfonylphenyl)-2(5H)-furanone) | 23 | I |

TABLE I-continued

| | Example | Method |
|---|---|---|
| (3-(2-chlorophenyl)-4-(4-(methylsulfonyl)phenyl)furan-2(5H)-one) | 24 | I |
| (3-(2-bromo-4-fluorophenyl)-4-(4-(methylsulfonyl)phenyl)furan-2(5H)-one) | 25 | I |
| (3-(2-bromo-4-chlorophenyl)-4-(4-(methylsulfonyl)phenyl)furan-2(5H)-one) | 26 | I |
| (3-(2-fluoro-4-chlorophenyl)-4-(4-(methylsulfonyl)phenyl)furan-2(5H)-one) | 27 | I |
| (3-(3-bromo-4-fluorophenyl)-4-(4-(methylsulfonyl)phenyl)furan-2(5H)-one) | 28 | I |
| (3-(3-chlorophenyl)-4-(4-(methylsulfonyl)phenyl)furan-2(5H)-one) | 29 | I |
| (3-(2-chloro-4-fluorophenyl)-4-(4-(methylsulfonyl)phenyl)furan-2(5H)-one) | 30 | I |
| (3-(2,4-dichlorophenyl)-4-(4-(methylsulfonyl)phenyl)furan-2(5H)-one) | 31 | I |
| (3-(3,4-dichlorophenyl)-4-(4-(methylsulfonyl)phenyl)furan-2(5H)-one) | 32 | I |
| (3-(2,6-dichlorophenyl)-4-(4-(methylsulfonyl)phenyl)furan-2(5H)-one) | 33 | I |

TABLE I-continued
| | Example | Method |
|---|---|---|
| 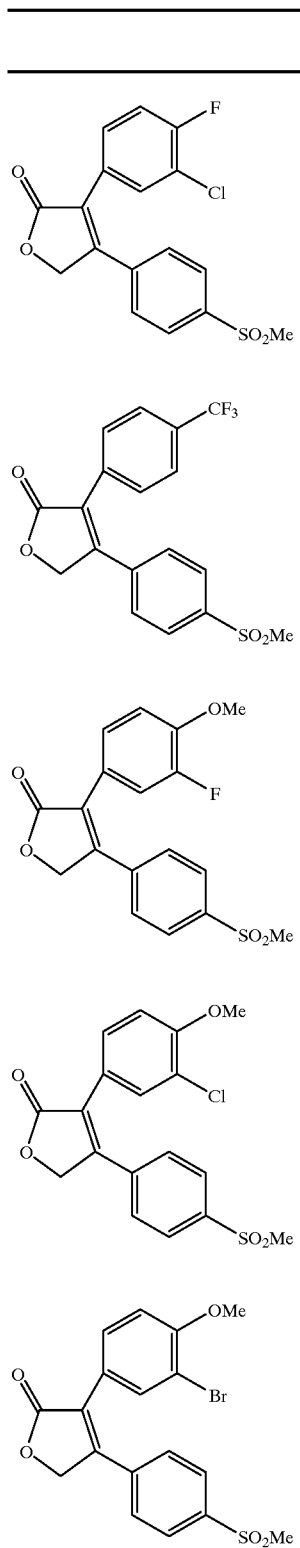 | 34 | I |
| | 35 | I |
| | 36 | I |
| | 37 | I |
| | 38 | I |
TABLE I-continued
| | Example | Method |
|---|---|---|
| 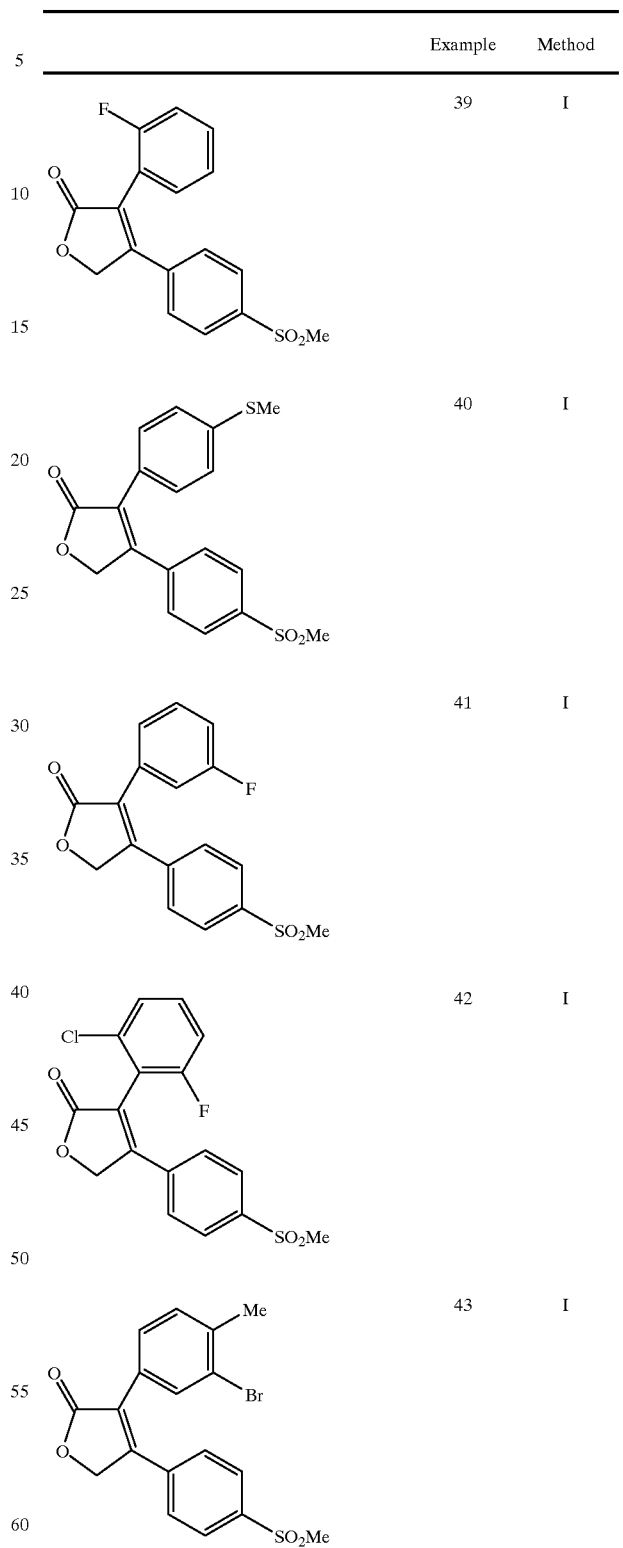 | 39 | I |
| | 40 | I |
| | 41 | I |
| | 42 | I |
| | 43 | I |

TABLE I-continued

| | Example | Method |
|---|---|---|
| 3-(4-bromo-2-fluorophenyl)-4-(4-(methylsulfonyl)phenyl)furan-2(5H)-one | 44 | I |
| 3-(3,4-dibromophenyl)-4-(4-(methylsulfonyl)phenyl)furan-2(5H)-one | 45 | I |
| 3-(4-chloro-3-fluorophenyl)-4-(4-(methylsulfonyl)phenyl)furan-2(5H)-one | 46 | I |
| 3-(4-bromo-3-fluorophenyl)-4-(4-(methylsulfonyl)phenyl)furan-2(5H)-one | 47 | I |
| 3-(4-bromo-2-chlorophenyl)-4-(4-(methylsulfonyl)phenyl)furan-2(5H)-one | 48 | I |

TABLE I-continued

| | Example | Method |
|---|---|---|
| 3-(naphthalen-2-yl)-4-(4-(methylsulfonyl)phenyl)furan-2(5H)-one | 49 | I |
| 3-(quinolin-7-yl)-4-(4-(methylsulfonyl)phenyl)furan-2(5H)-one | 50 | I |
| 3-(3,4-dichlorophenyl)-4-(4-(sulfamoyl)phenyl)furan-2(5H)-one | 51 | I |
| 3-(3,4-difluorophenyl)-4-(4-(sulfamoyl)phenyl)furan-2(5H)-one | 52 | I |
| 3-(3-chloro-4-methoxyphenyl)-4-(4-(sulfamoyl)phenyl)furan-2(5H)-one | 53 | I |

TABLE I-continued

| Example | Method |
|---|---|
| 54 | I |
| 55 | H |
| 56 | L + M |
| 57 | L + M |
| 58 | L + M |
| 59 | L + M |
| 60 | L + M |

TABLE II

TABLE II-continued
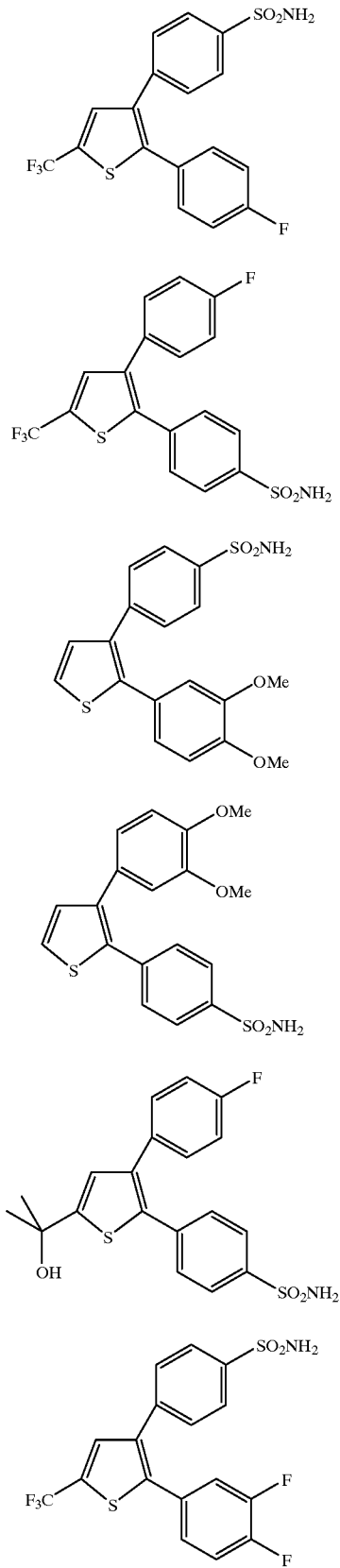
TABLE II-continued
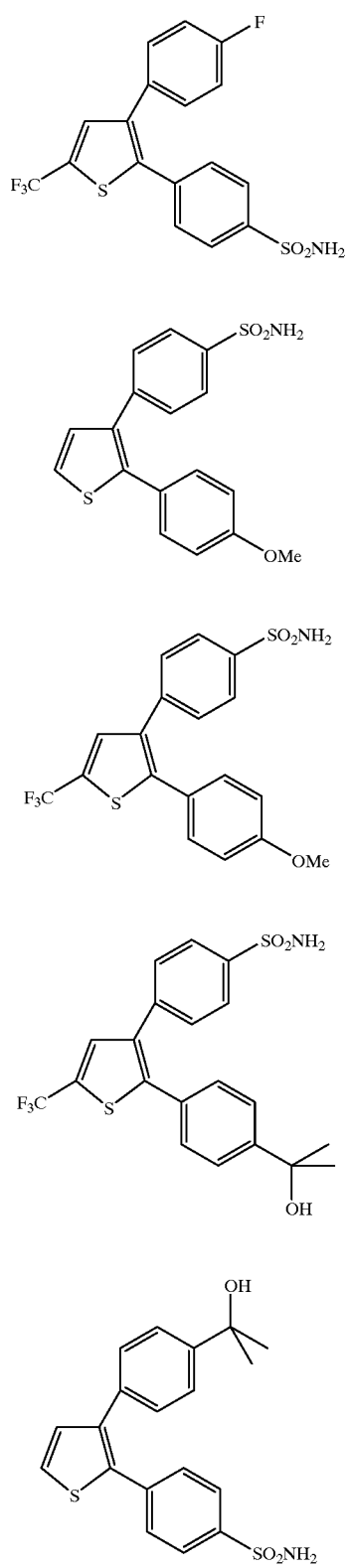

TABLE II-continued
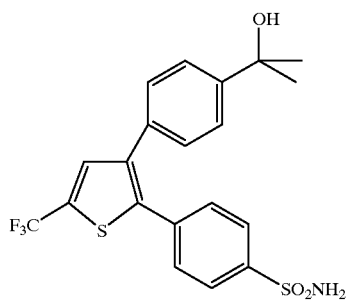
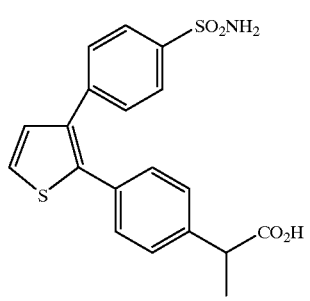
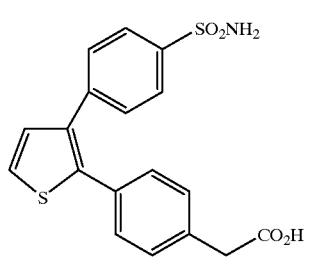
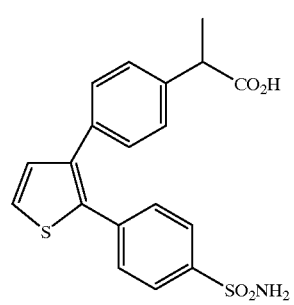
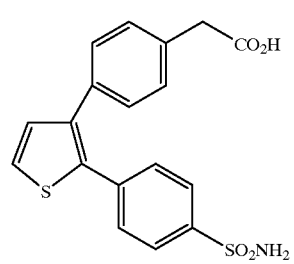
TABLE II-continued
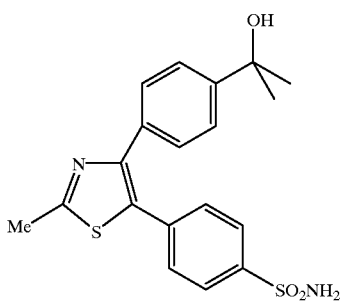
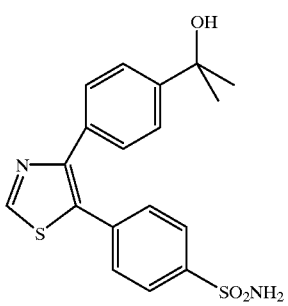
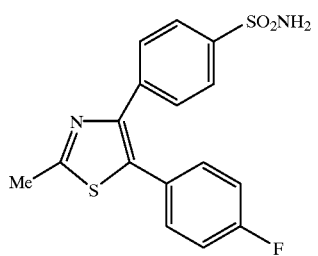
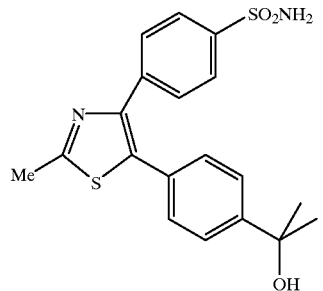
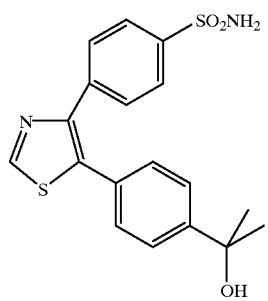

TABLE II-continued
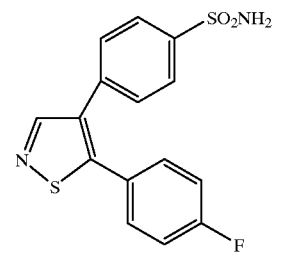
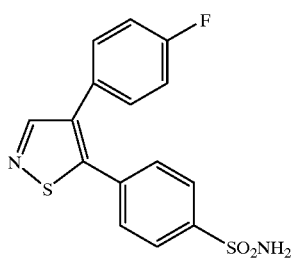
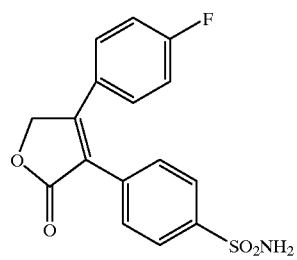
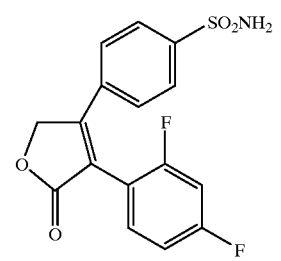
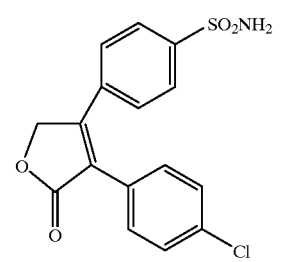
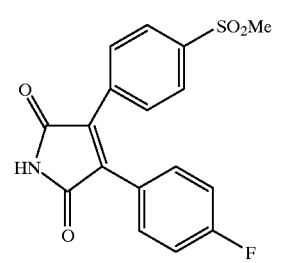
TABLE II-continued
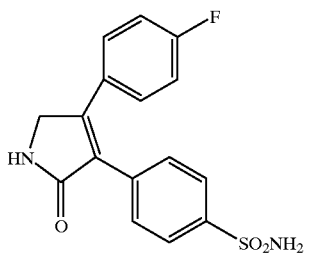
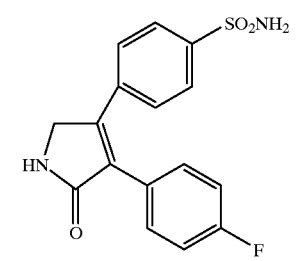
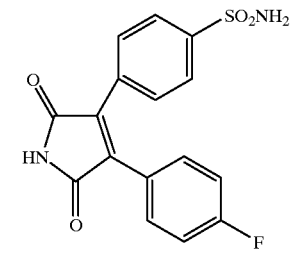
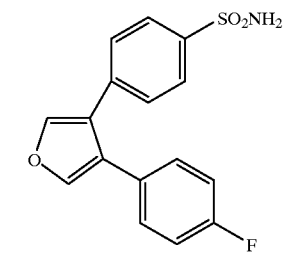
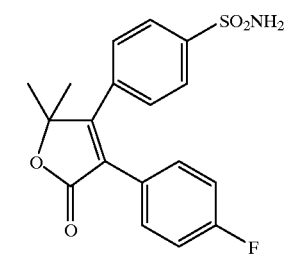
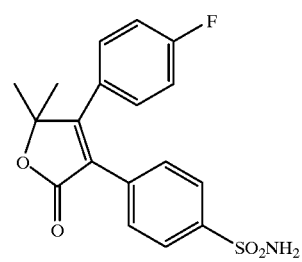

TABLE II-continued
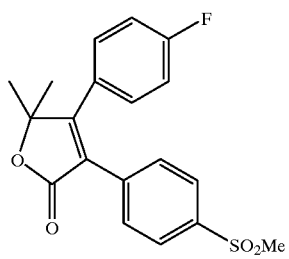
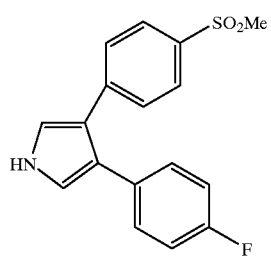
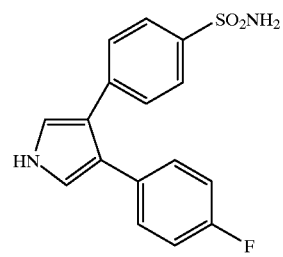
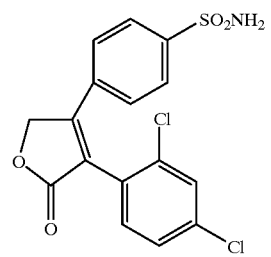
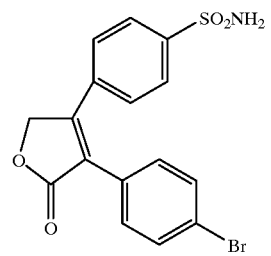
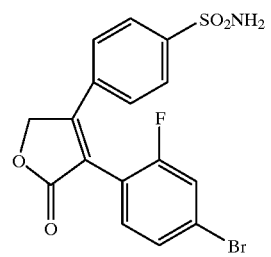
TABLE II-continued
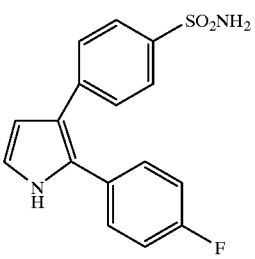
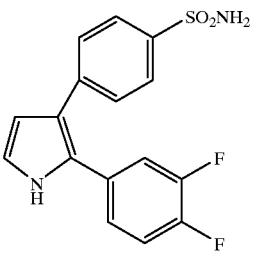
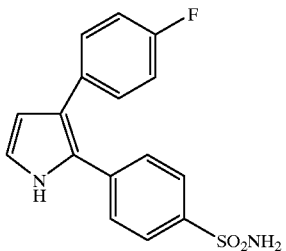
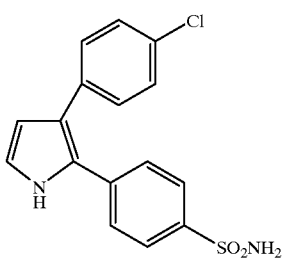
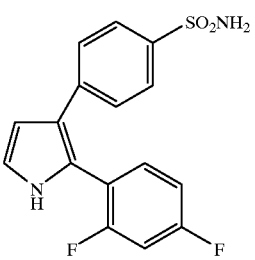
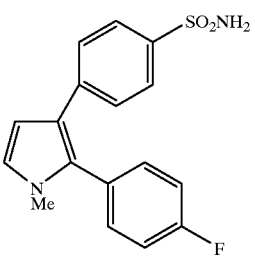

TABLE II-continued
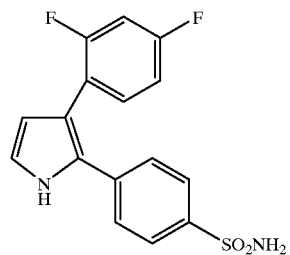
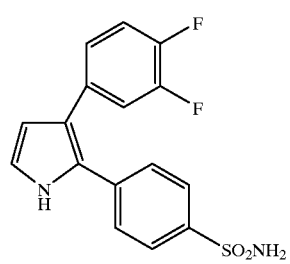
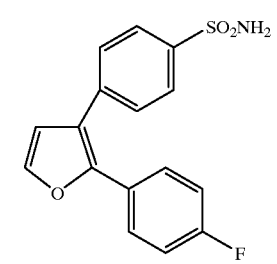
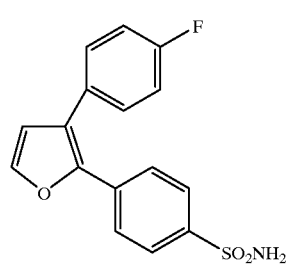
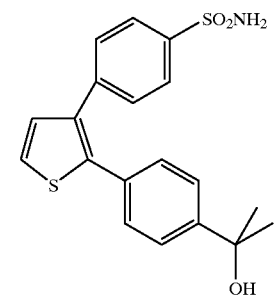
TABLE II-continued
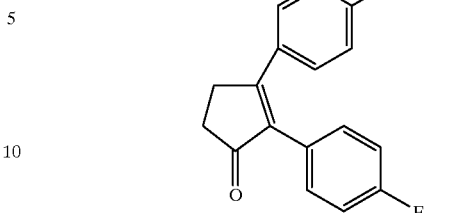
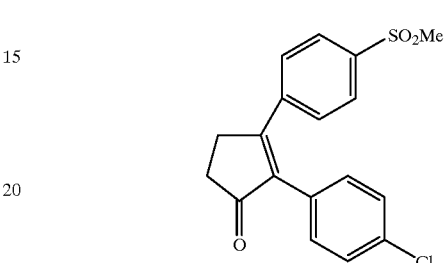
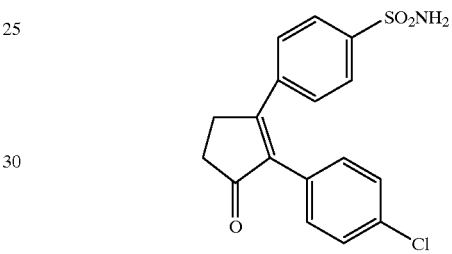
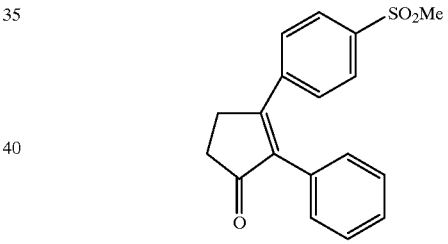
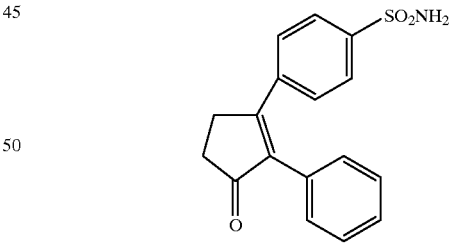
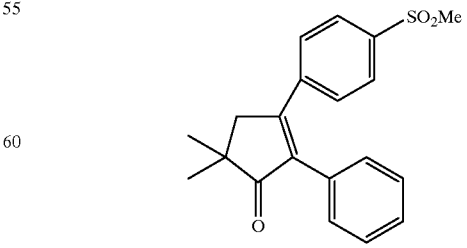

TABLE II-continued
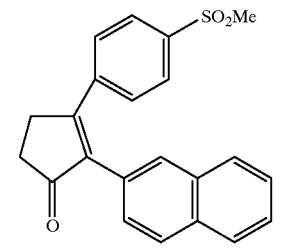
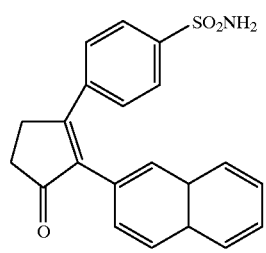
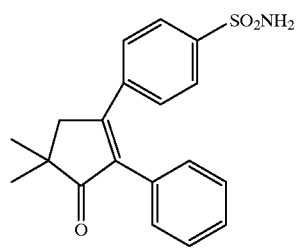
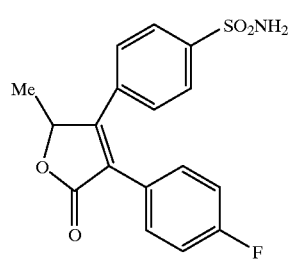
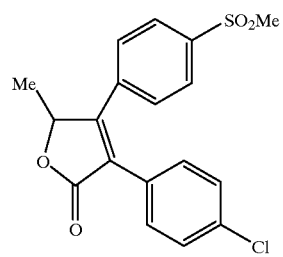
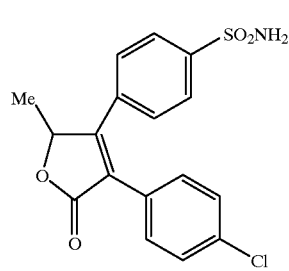
TABLE II-continued
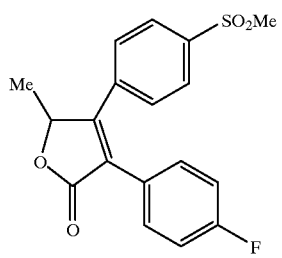
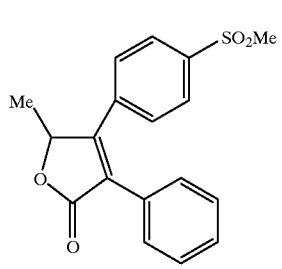
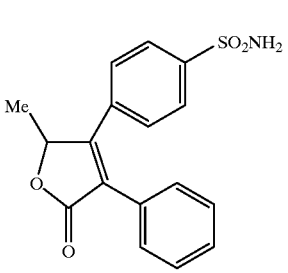
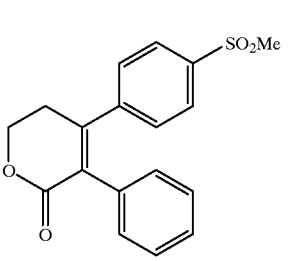
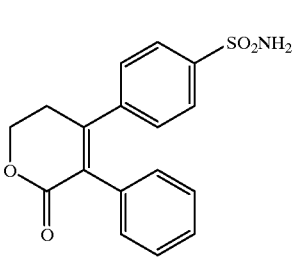
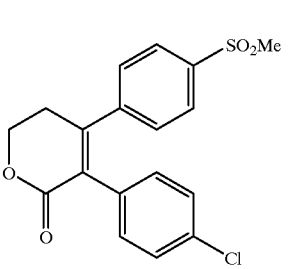

TABLE II-continued
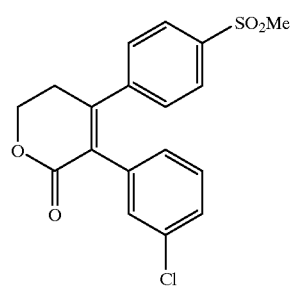
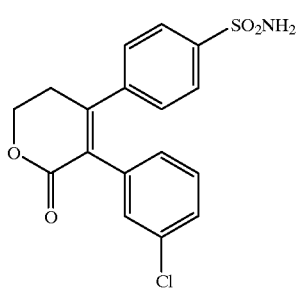
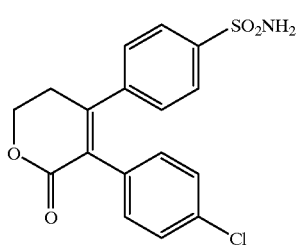
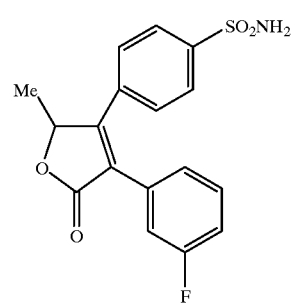
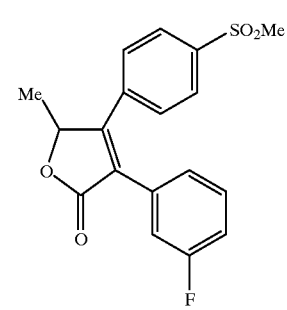
TABLE II-continued
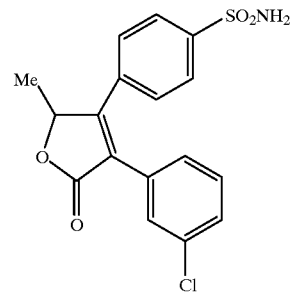
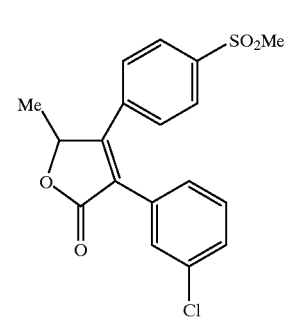
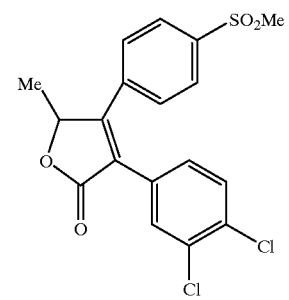
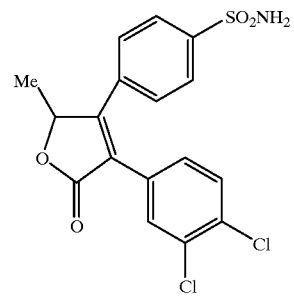
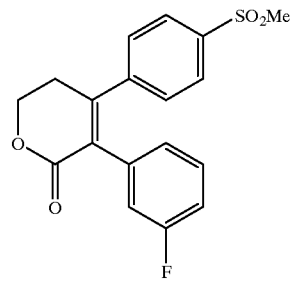

TABLE II-continued
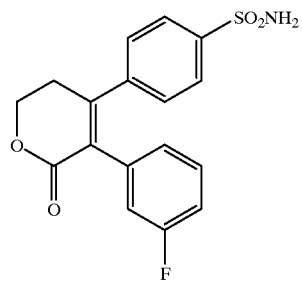
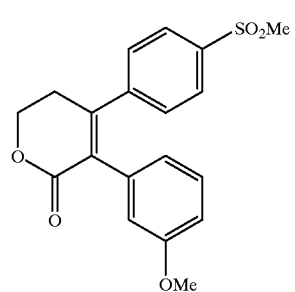
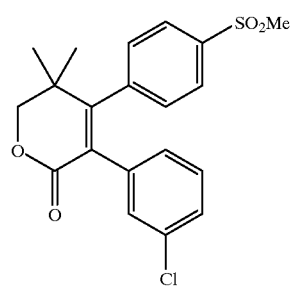
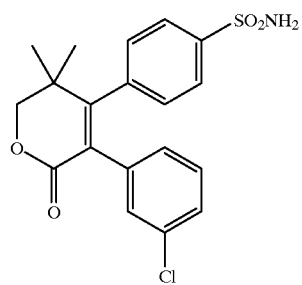
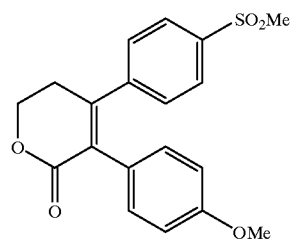
TABLE II-continued
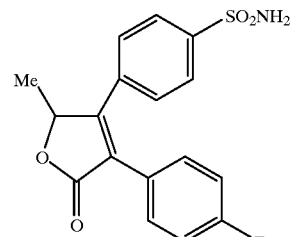
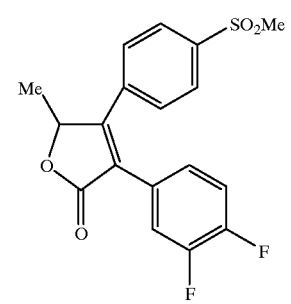
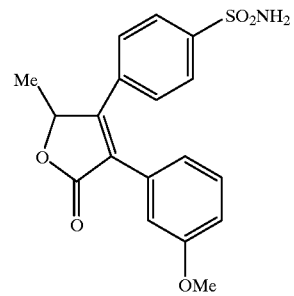
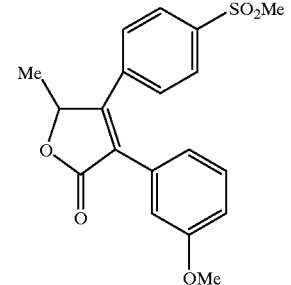
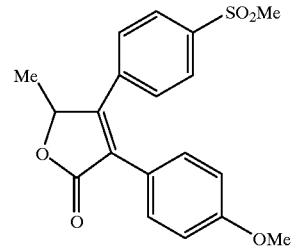

TABLE II-continued

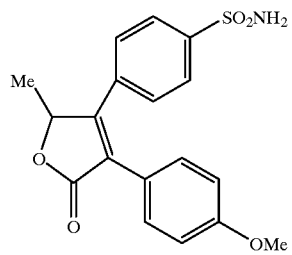

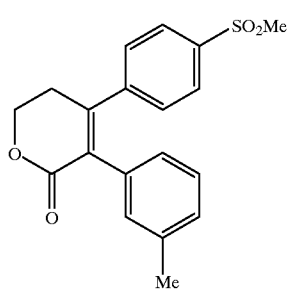

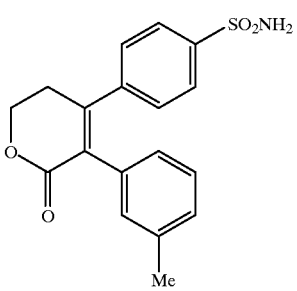

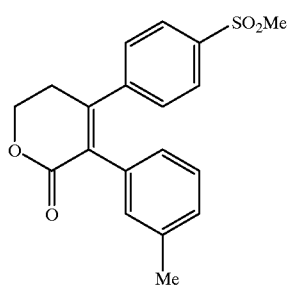

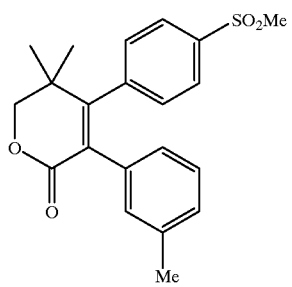

TABLE II-continued

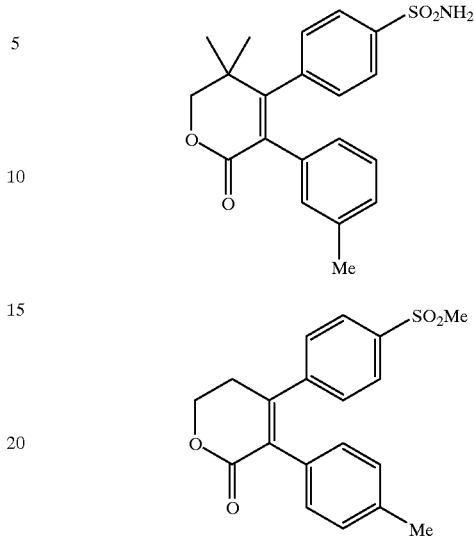

Assays for Determining Biological Activity

The compound of Formula I can be tested using the following assays to determine their cyclooxygenase-2 inhibiting activity.

Inhibition of Cyclooxygenase Activity

Compounds were tested as inhibitors of cyclooxygenase activity in whole cell and microsomal cyclooxygenase assays. Both of these assays measured prostaglandin $E_2$ ($PGE_2$) synthesis in response to arachidonic acid, using a radioimmunoassay. Cells used for whole cell assays, and from which microsomes were prepared for microsomal assays, were human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate addition. $IC_{50}$ values represent the concentration of putative inhibitor required to return $PGE_2$ synthesis to 50% of that obtained as compared to the uninhibited control. Representative results are shown in Table III.

Representative Rat Paw Edema Assay—Protocol

Male Sprague-Dawley rats (150–200 g) were fasted overnight and were given po either vehicle (5% tween 80 or 1% methocel) or a test compound at 9–10 am. One hr later, a line was drawn using a permanent marker at the level above the ankle in one hind paw to define the area of the paw to be monitored. The paw volume ($V_{Oh}$) was measured using a plethysmometer (Ugo-Basile, Italy) based on the principle of water displacement. The animals were then injected subplantarly with 50 ul of a 1% carrageenan solution in saline (FMC Corp, Maine) into the paw using an insulin syringe with a 25-gauge needle (i.e. 500 ug carrageenan per paw). Three hr later, the paw volume ($V_{3h}$) was measured and the increases in paw volume ($V_{3h}$-$V_{Oh}$) were calculated. The animals were euthanized by $CO_2$ aphyxiation and the absence or presence of stomach lesions scored. Stomach scores were expressed as the sum of total lesions in mm. Paw edema data were compared with the vehicle-control group and percent inhibition calculated taking the values in the control group as 100%. Since a maximum of 60–70% inhibition (paw edema) was obtained with standard NSAIDs, $ED_{30}$ values were used for comparison. All treatment groups were coded to eliminate observer bias. With this protocol, the $ED_{30}$ for Indomethacin is 1.0 mg/kg. Representative results are shown in Table IV.

TABLE III*

| | Whole Cells | | | Microsomes | | |
|---|---|---|---|---|---|---|
| Example | Conc. (nM) | COX-2 % inhib. | COX-1 % inhib. | Conc. (nM) | COX-2 % inhib. | COX-1 % inhib. |
| 1 | 100 | 96 | 12 | 100 | 53 | 8 |
| 2 | 10 | 69 | 0 | 10 | 49 | 25 |
| 3 | 10 | 42 | | 10 | 33 | 19 |
| 3 | 100 | 100 | | 100 | 76 | 12 |
| 4 | | | | 10 | 47 | 2 |
| 5 | 10 | 0 | 0 | 10 | 43 | 31 |
| 6 | 100 | 78 | | 100 | 19 | 16 |
| 7 | 100 | 74 | 0 | 1000 | 58 | 16 |
| 8 | 10 | 41 | | | | |
| 8 | 100 | 89 | | | | |
| 9 | 100 | 83 | | 100 | 37 | 9 |
| 10 | 100 | 95 | | 100 | 71 | 12 |
| 11 | 100 | 39 | | 100 | 46 | 7 |
| 12 | 100 | 54 | | | | |
| 13 | 10 | 41 | | 10 | 52 | 7 |
| 13 | 100 | 84 | | 10 | 58 | 10 |
| 14 | 10 | 73 | | 10 | 45 | 29 |
| 14 | 100 | 89 | | 100 | 63 | 0 |
| 14 | 1000 | 101 | | 1000 | 69 | 0 |
| 15 | 20 | 39 | | | | |
| 15 | 80 | 76 | | | | |
| 15 | 160 | 95 | | | | |
| 16 | 20 | 41 | | | | |
| 16 | 40 | 50 | | | | |
| 16 | 160 | 85 | | | | |
| 17 | 40 | 41 | | | | |
| 17 | 160 | 77 | | | | |
| 18 | 40 | 24 | | | | |
| 18 | 160 | 58 | | | | |
| 19 | 40 | 21 | | | | |
| 19 | 160 | 59 | | | | |
| 20 | 10 | 70 | | | | |
| 20 | 40 | 91 | | | | |
| 21 | 10 | 50 | | | | |
| 21 | 40 | 94 | | | | |
| 22 | 20 | 39 | | | | |
| 22 | 160 | 98 | | | | |
| 23 | 20 | 50 | | | | |
| 23 | 160 | 88 | | | | |
| 24 | 40 | 43 | | | | |
| 24 | 160 | 78 | | | | |
| 25 | 160 | 40 | | | | |
| 26 | 80 | 27 | | | | |
| 26 | 160 | 39 | | | | |
| 27 | 20 | 38 | | | | |
| 27 | 160 | 97 | | | | |
| 28 | 20 | 48 | | | | |
| 28 | 160 | 69 | | | | |
| 29 | 20 | 78 | | | | |
| 29 | 160 | 85 | | | | |
| 30 | 160 | 30 | | | | |
| 31 | 20 | 49 | | | | |
| 31 | 160 | 87 | | | | |
| 32 | 5 | 43 | | | | |
| 32 | 10 | 73 | | | | |
| 32 | 40 | 92 | | | | |
| 32 | 80 | 99 | | | | |
| 33 | 160 | 6 | | | | |
| 34 | 10 | 30 | | | | |
| 34 | 40 | 80 | | | | |
| 34 | 160 | 102 | | | | |
| 35 | 20 | 32 | | | | |
| 35 | 40 | 57 | | | | |
| 35 | 160 | 83 | | | | |
| 36 | 10 | 11 | | | | |
| 36 | 40 | 50 | | | | |
| 36 | 160 | 89 | | | | |
| 37 | 10 | 53 | | | | |
| 37 | 40 | 82 | | | | |
| 37 | 160 | 93 | | | | |
| 38 | 10 | 25 | | | | |
| 38 | 40 | 63 | | | | |
| 38 | 160 | 88 | | | | |
| 39 | 10 | 17 | | | | |
| 39 | 160 | 84 | | | | |
| 40 | 10 | 43 | | | | |
| 40 | 40 | 72 | | | | |
| 40 | 160 | 96 | | | | |
| 41 | | | | | | |
| 41 | | | | | | |
| 42 | 20 | 10 | | | | |
| 42 | 160 | 44 | | | | |
| 43 | 10 | 78 | | | | |
| 43 | 40 | 101 | | | | |
| 44 | 20 | 14 | | | | |
| 44 | 40 | 55 | | | | |
| 44 | 160 | 106 | | | | |
| 45 | 10 | 16 | | | | |
| 45 | 40 | 61 | | | | |
| 45 | 160 | 101 | | | | |
| 46 | 10 | 76 | | | | |
| 46 | 40 | 94 | | | | |
| 46 | 160 | 97 | | | | |
| 47 | 10 | 61 | | | | |
| 47 | 40 | 74 | | | | |
| 47 | 160 | 101 | | | | |
| 48 | 10 | 7 | | | | |
| 48 | 160 | 47 | | | | |
| 49 | 10 | 53 | | | | |
| 49 | 40 | 91 | | | | |
| 49 | 80 | 99 | | | | |
| 50 | 80 | 42 | | | | |
| 51 | 5 | 49 | | | | |
| 51 | 20 | 95 | | | | |
| 51 | 40 | 102 | | | | |
| 52 | 10 | 50 | | | | |
| 52 | 40 | 82 | | | | |
| 52 | 160 | 102 | | | | |
| 53 | 10 | 54 | | | | |
| 53 | 40 | 96 | | | | |
| 53 | 160 | 102 | | | | |
| 54 | 10 | 81 | | | | |
| 54 | 80 | 91 | | | | |
| 54 | 160 | 99 | | | | |
| 55 | 10 | 48 | | | | |
| 55 | 80 | 59 | | | | |
| 55 | 160 | 65 | | | | |

*In the whole cell assay Ibuprofen has an IC50 for COX-1 of 1000 nM, and an IC50 for COX-2 of 3000 nM. Similarly, Indomethacin has an IC50 for COX-1 of 100 nM, and an IC50 for COX-2 of 10 nM.

TABLE IV

| ED30 (mg/kg) | STRUCTURE |
|---|---|
| ~3.00 | 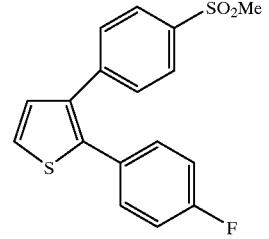 |

TABLE IV-continued

| ED30 (mg/kg) | STRUCTURE |
|---|---|
| >10.00 | 3,4-bis(aryl)thiophene with 4-SO₂Me phenyl and 4-F phenyl |
| 1.40 | 2,3-bis(aryl)thiophene with 4-SO₂NH₂ phenyl and 4-F phenyl |
| 2.80 (in 1% methocel) 0.72 | 3,4-bis(aryl)furan-2(5H)-one with 4-SO₂Me phenyl and 4-F phenyl |
| 0.43 | 2,3-bis(aryl)cyclopent-2-enone with 4-SO₂Me phenyl and 4-F phenyl |
| ~3.00 | 5-(2-hydroxypropan-2-yl)-2,3-bis(aryl)thiophene with 4-SO₂NH₂ phenyl and 4-F phenyl |
| >3.00 3.00 | 3,4-bis(aryl)thiophene with 4-SO₂NH₂ phenyl and 4-F phenyl |

TABLE IV-continued

| ED30 (mg/kg) | STRUCTURE |
|---|---|
| 1.10 | 4,5-bis(aryl)isothiazole with 4-SO₂Me phenyl and 4-F phenyl |
| <0.30 | 2,3-bis(aryl)thiophene with 4-F phenyl and 4-SO₂NH₂ phenyl |
| 0.42 | 5,5-dimethyl-3,4-bis(aryl)furan-2(5H)-one with 4-SO₂Me phenyl and 4-F phenyl |
| 0.034 | 3,4-bis(aryl)furan-2(5H)-one with 4-SO₂NH₂ phenyl and 4-F phenyl |
| 2.03 | 3,4-bis(aryl)furan-2(5H)-one with 4-SO₂Me phenyl and 2,4-difluorophenyl |
| 1.49 | bicyclic fused furanone with 4-SO₂Me phenyl and 2,6-difluorophenyl |

TABLE IV-continued

| ED30 (mg/kg) | STRUCTURE |
|---|---|
| 0.35 | 3-(3,4-difluorophenyl)-4-(4-methylsulfonylphenyl)-2(5H)-furanone |
| 0.33 | 3-(4-bromophenyl)-4-(4-methylsulfonylphenyl)-2(5H)-furanone |
| 0.90 | 3-(4-chlorophenyl)-4-(4-methylsulfonylphenyl)-2(5H)-furanone |
| 0.38 | 3-phenyl-4-(4-methylsulfonylphenyl)-2(5H)-furanone |
| 0.88 | 3-(2-bromo-4-chlorophenyl)-4-(4-methylsulfonylphenyl)-2(5H)-furanone |
| 0.47 | 3-(2-fluoro-4-chlorophenyl)-4-(4-methylsulfonylphenyl)-2(5H)-furanone |
| 0.71 | 3-(3-chlorophenyl)-4-(4-methylsulfonylphenyl)-2(5H)-furanone |
| ~1.00 | 3-(3-bromo-4-fluorophenyl)-4-(4-methylsulfonylphenyl)-2(5H)-furanone |
| 1.85 | 3-(2,4-dichlorophenyl)-4-(4-methylsulfonylphenyl)-2(5H)-furanone |
| 0.22 / 0.23 | 3-(3,4-dichlorophenyl)-4-(4-methylsulfonylphenyl)-2(5H)-furanone |
| 0.43 | 3-(3-chloro-4-fluorophenyl)-4-(4-methylsulfonylphenyl)-2(5H)-furanone |
| 2.17 | 3-(4-trifluoromethylphenyl)-4-(4-methylsulfonylphenyl)-2(5H)-furanone |

TABLE IV-continued

| ED30 (mg/kg) | STRUCTURE |
|---|---|
| 0.81 | 4-(4-methylsulfonylphenyl)-3-(3-fluoro-4-methoxyphenyl)-2(5H)-furanone |
| 0.68 | 4-(4-methylsulfonylphenyl)-3-(3-chloro-4-methoxyphenyl)-2(5H)-furanone |
| 0.16 | 4-(4-methylsulfonylphenyl)-3-(2-naphthyl)-2(5H)-furanone |
| ~1.00 | 4-(4-methylsulfonylphenyl)-3-(4-methylthiophenyl)-2(5H)-furanone |
| 0.33 | 4-(4-methylsulfonylphenyl)-3-(3-fluorophenyl)-2(5H)-furanone |
| 0.46 | 4-(4-methylsulfonylphenyl)-3-(2-bromo-4-methylphenyl)-2(5H)-furanone |
| 0.76 | 4-(4-methylsulfonylphenyl)-3-(3,4-dibromophenyl)-2(5H)-furanone |
| 0.48 | 4-(4-sulfamoylphenyl)-3-(3,4-difluorophenyl)-2(5H)-furanone |
| 0.46 | 4-(4-sulfamoylphenyl)-3-(3,4-dichlorophenyl)-2(5H)-furanone |
| 0.26 | 4-(4-methylsulfonylphenyl)-3-(3-fluoro-4-chlorophenyl)-2(5H)-furanone |

TABLE IV-continued

| ED30 (mg/kg) | STRUCTURE |
|---|---|
| 0.55 | 4-(4-methylsulfonylphenyl)-3-(4-bromo-3-fluorophenyl)furan-2(5H)-one |
| 0.25 | 5,5-dimethyl-4-(4-methylsulfonylphenyl)-3-(3-chlorophenyl)furan-2(5H)-one |
| 0.1–.3 | 5,5-dimethyl-4-(4-methylsulfonylphenyl)-3-(2-naphthyl)furan-2(5H)-one |
| ~0.10 | 5,5-dimethyl-4-(4-methylsulfonylphenyl)-3-(3,4-difluorophenyl)furan-2(5H)-one |
| 0.13 | 5,5-dimethyl-4-(4-methylsulfonylphenyl)-3-(3,4-dichlorophenyl)furan-2(5H)-one |
| 0.07 | 5,5-dimethyl-4-(4-methylsulfonylphenyl)-3-(4-chlorophenyl)furan-2(5H)-one |

The invention will now be illustrated by the following non-limiting examples in which, unless stated otherwise:

(i) all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:
Ac=acetyl
Bn=benzyl
DBU=1,8-diazabicyclo[5.4.0]undec-7-ene
DIBAL=diisobutylaluminum hydride
DMAP=4-(dimethylamino)pyridine
DMF=N,N-dimethylformamide
Et$_3$N=triethylamine
LDA=lithium diisopropylamide
m-CPBA=metachloroperbenzoic acid
MMPP=monoperoxyphtalic acid
MPPM=monoperoxyphthalic acid, magnesium salt 6H$_2$O
Ms=methanesulfonyl=mesyl=SO$_2$Me
MsO=methanesulfonate=mesylate
NSAID=non-steroidal anti-inflammatory drug
OXONE®=2KHSO$_5$.KHSO$_4$.K$_2$SO$_4$
PCC=pyridinium chlorochromate
PDC=pyridinium dichromate Ph=phenyl
Phe=benzenediyl
Pye=pyridinediyl
r.t.=room temperature
rac.=racemic
SAM=aminosulfonyl or sulfonamide or $SO_2NH_2$
TBAF=tetra-n-butylammonium fluoride
Th=2- or 3-thienyl
TFAA=trifluoroacetic acid anhydride
THF=tetrahydrofuran
Thi=thiophenediyl
TLC=thin layer chromatography
TMS-CN=trimethylsilyl cyanide
Tz=1H (or 2H)-tetrazol-5-yl
$C_3H_5$=allyl
Alkyl Group Abbreviations
 Me=methyl
 Et=ethyl
 n-Pr=normal propyl
 i-Pr=isopropyl
 n-Bu=normal butyl
 i-Bu=isobutyl
 s-Bu=secondary butyl
 t-Bu=tertiary butyl
 c-Pr=cyclopropyl
 c-Bu=cyclobutyl
 c-Pen=cyclopentyl
 c-Hex=cyclohexyl

EXAMPLE 1

3-(4-Aminosulfonyl)phenyl)-2-(4-fluorophenyl)-5-(2-hydroxy-2-propyl)thiophene

Step 1

1-(4-Fluorophenyl)-2-(4-(methylthio)phenyl)ethanone

To 4-fluorobenzaldehyde (5.40 g) in 1,2-dichloroethane (43.50 mL) were added TMS-CN (4.32 g) and $ZnI_2$ (44 mg). After 0.5 h at r.t., the solvent was removed in vacuo. To the resulting TMS cyanohydrin (9.20 g) in THF (42.0 mL) at −78° C. was added dropwise a solution of LDA 0.51M in THF (88.9 mL). After a period of 0.5 h, a THF solution (30.0 mL) of 4-(chloromethyl)thioanisole (9.93 g) was added dropwise over 0.5 h. After 18 h at +5° C., the resulting mixture was treated with TBAF (57.5 mL) followed by a 25% aqueous solution of $NH_4OAc$ (100 mL) and extracted with EtOAc (2×150 mL). After evaporation, a 10:1 mixture of $Et_2O$ and hexane (200 mL) was added to the crude ketone. After stirring for 10 h and filtration, the title product was obtained as a solid by filtration (2.40 g).

$^1$H NMR ($CD_3COCD_3$): δ2.45 (3H, s), 4.34 (2H, s), 7.19–7.29 (6H, m), 8.14 (2H, q).

Step 2

Cis,trans-3-chloro-3-(4-fluorophenyl)-2-(4-(methylthio)phenyl)propenal

To a solution of 1-(4-fluorophenyl)-2-(4-(methylthio) phenyl ethanone (2.50 g) in 1,2-dichloroethane (27.0 mL) were introduced the Vilsmeier reagent (Aldrich catalog, 1992–1993) 3.3M (11.6 mL) and DMAP (1.17 g). After a period of 4 h at 80° C., the reaction mixture was extracted with EtOAc and 25% aqueous solution of $NH_4OAc$. After evaporation in vacuo and drying for a few hours, the title product was used as such for the next step.

$^1$H NMR ($CD_3COCD_3$): δ2.40 and 2.48 (3H, 2s), 6.90–7.80 (8H, m), 9.55 (1H, s).

Step 3

5-(4-Fluorophenyl)-4-(4-(methylthio)phenyl)thiophene-2-carboxylic acid methyl ester To a solution of cis,trans 3-chloro-3-(4-fluorophenyl)-2-(4-(methylthio)phenyl)propenal (3.00 g) in pyridine (12.0 mL) were added methyl thioglycolate (1.16 mL) and $Et_3N$ (4.09 mL). The resulting mixture was then heated at 80° C. for 2 h. After extraction with EtOAc and washing with 3N HCl, the title product was purified by flash chromatography (30% EtOAc in hexane) (2.00 g).

$^1$H NMR ($CD_3COCD_3$): δ2.48 (3H, s), 3.88 (3H, s), 7.11 (2H, t), 7.21 (4H, s), 7.37 (2H, q), 7.80 (1H, s).

Step 4

5-(4-Fluorophenyl)-4-(4-(methylsulfinyl)phenyl)thiophene-2-carboxylic acid methyl ester To a solution of 5-(4-fluorophenyl)-4-(4-(methylthio) phenyl)-thiophene-2-carboxylic acid methyl ester (5.60 g) in $CH_2Cl_2$ (84.0 mL) at 0° C. was added portionwise m-CPBA 50 to 60% (5.39 g). After TLC showed completion (50% EtOAc in hexane), the reaction mixture was extracted with saturated $NaHCO_3$, dried over $Na_2SO_4$, filtered and evaporated to dryness to provide the title compound as a white foam (5.00 g).

$^1$H NMR ($CD_3COCD_3$): δ2.75 (3H, s), 3.92 (3H, s), 7.15 (2H, t), 7.40 (2H, q), 7.52 (2H, d), 7.66 (2H, d), 7.90 (1H, s).

Step 5

4-(4-(Aminosulfonyl)phenyl)-5-(4-fluorophenyl)thiophene-2-carboxylic acid methyl ester 5-(4-Fluorophenyl)-4-(4-(methylsulfinyl)phenyl)thiophene-2-carboxylic acid methyl ester (0.500 g) was dissolved in TFAA (10.0 mL) and refluxed for 0.5 h. The solvent was then removed in vacuo and the resulting residue was co-evaporated 10 times with a $Et_3$N-MeOH solution (1:1) (100.0 mL) to provide a viscous oil after pumping for a few hours. The oil was dissolved in HOAc (10.0 mL) and treated at +10° C. with $Cl_2$ in HOAc (1.9M) (3.5 mL). After 20 min., the solvent was removed under reduced pressure and after pumping, THF (20.0 mL) was added to the resulting mass of product. After bubbling $NH_3$ through for a few minutes at 0° C., the reaction mixture was stirred for 0.5 h at r.t. After extraction with EtOAc-25% $NH_4OAc$ solution and flash chromatography (30 to 40% EtOAc in hexane), the title product was obtained as a white solid (0.210 g).

$^1$H NMR ($CD_3COCD_3$): δ3,90 (3H, s), 6.55 (2H, bs), 7.13 (2H, t), 7.40 (2H, q), 7.46 (2H, d), 7.83 (2H, d), 7.90 (1H, s).

Step 6

3-(4-Aminosulfonyl)phenyl)-2-(4-fluorophenyl)-5-(2-hydroxy-2-propyl)thiophene

To 4-(4-aminosulfonyl)phenyl)-5-(4-fluorophenyl) thiophene-2-carboxylic acid methyl ester (0.460 g) in THF (5.70 mL) at 0° C. was added MeMgBr (1.4M) in toluene-THF solution (5.00 mL). The mixture was then stirred at r.t.

for a few hours. The reaction was quenched by the addition of 25% NH$_4$OAc solution, extracted with EtOAc and dried over with Na$_2$SO$_4$. The title compound was purified by flash chromatography (40 to 50% EtOAc in hexane) (0.300 g).

$^1$H NMR (CD$_3$COCD$_3$): δ1.65 (6H, s), 4.52 (1H, s), 6.55 (2H, bs), 7.09 (3H, m), 7.34 (2H, dd), 7.30 (2H, m), 7.43 (2H, d), 7.82 (2H, d). Anal. calcd. for C$_{19}$H$_{18}$FNO$_3$S$_2$; C, 58.31; H, 4.60; N, 3.58. Found: C, 57.94; H, 4.66; N, 3.44

EXAMPLE 2

3-(4-(Aminosulfonyl)phenyl)-2-(4-fluorophenyl) thiophene

Step 1

4(4-(Aminosulfonyl)phenyl)-5-(4-fluorophenyl) thiophene-2-carboxylic acid

To a solution of 4-(4-(aminosulfonyl)phenyl)-5-(4-fluorophenyl)thiophene-2-carboxylic acid methyl ester (Example 1, Step 5) (0.210 g) in THF (2.0 mL) were added MeOH (1.0 mL), NaOH 1N (1.0 mL) and a few drops of NaOH 10N. The resulting mixture was heated at 45° C. for 2 h and the reaction was then partitioned between EtOAc and HCl (3N) to provide the title product as a white solid (0.200 g).

$^1$H NMR (CD$_3$COCD$_3$) δ6.60 (2H, s), 7.15 (2H, t), 7.35 (2H, q), 7.45 (2H, d), 7.82 (2H, d), 7.87 (1H, s).

Step 2

3-(4-(Aminosulfonyl)phenyl)-2-(4-fluorophenyl) thiophene

To a solution of 3-(4-(aminosulfonyl)phenyl)-2-(4-fluorophenyl)thiophene-2-carboxylic acid (0.280 g) in quinoline (4.0 mL) was added Cu bronze (0.300 g). After 0.5 h at 180° C. under nitrogen, the reaction mixture was extracted with EtOAc and HCl 3N, dried over Na$_2$SO$_4$ and purified by flash chromatography (30% EtOAc in hexane) to give the title compound as a white solid (0.180 g).

$^1$H NMR (CD$_3$COCD$_3$): δ6.60 (2H, bs), 7.15 (2H, t), 7.29 (1H, d), 7.35 (2H, q), 7.45 (2H, d), 7.60 (1H, d), 7.83 (2H, d).

Anal. calcd for C$_{16}$H$_{12}$FNO$_2$S$_2$; C, 57.65; H, 3.60; N, 4.20.

Found: C, 57.62; H, 3.59; N, 4.15.

EXAMPLE 3

3-(4-(Aminosulfonyl)phenyl)-2-(4-fluorophenyl)-5-(2-propyl)thiophene $^1$H NMR (CD$_3$COCD$_3$) δ1.40 (6H, d), 3.25 (1H, septuplet), 6.58 (2H, bs), 7.05 (1H, s), 7.15 (2H, t), 7.32 (2H, dd), 7.46 (2H, d), 7.80 (2H, d).

Anal. calcd. for C$_{19}$H$_{18}$FNO$_2$S$_2$. C, 60.80; H, 4.80; N, 3.73.

Found: C, 60.59; H, 4.45; N, 3.60.

EXAMPLE 4

3-(4-(Aminosulfonyl)phenyl)-2-cyclohexylthiophene $^1$H NMR (CD$_3$)$_2$CO) δ1.24–1.40 (3H, m), 1.40–1.56 (2H, m), 1.65–1.85 (3H, m), 1.90–2.0 (2H, m), 3.18 (1H, m), 6.58 (2H, bs), 7.05 (1H, d), 7.37 (1H, d), 7.58 (2H, d), 7.97 (2H, d).

EXAMPLE 5

5-(4-Carboxyphenyl)-4-(4-(methylsulfonyl)phenyl) thiophene-2-carboxylic acid

Step 1

4-(2-(4-Methylthiophenyl)-1-oxo-ethyl)benzoic acid methyl ester

To methyl 4-formylbenzoate (10.30 g) in 1,2-dichloroethane at r.t. were added TMS-CN (6.58 mL) and ZnI$_2$ (2.00 g), after 0.5 h at r.t., the solvent was removed in vacuo. To the resulting TMS cyanohyrin (5.00 g) in THF (22.0 mL) at −78° C. was added dropwise a solution of LDA 0.87 M in THF (26.2 mL). After a period of 0.5 h, a THF solution (10.0 mL) of 4-(chloromethyl)thioanisole was added dropwise over 0.5 h. The temperature was then brought slowly to −20° C. then to 5° C. for 2 h and TBAF 1M in THF (50.0 mL) was added. After the addition of 25% aqueous solution of NH$_4$OAc, the reaction mixture was extracted with EtOAc, dried over NASO$_4$, evaporated in vacuo and purified by flash chromatography (20 to 30% EtOAc in hexane) to afford the title compound as a white solid (7.00 g).

Step 2

4-(1-Oxo-2-(4-(methylsulfonyl)phenyl)ethyl) benzoic acid methyl ester

To 7.10 g of 4-(2-(4-methylthiophenyl)-1-oxo-ethyl) benzoic acid methyl ester in MeOH (100 mL) was added oxone (21.0 g) in H$_2$O (20.0 mL) at 0° C. After a few hours at r.t., the reaction mixture was extracted with EtOAc and H$_2$O to afford after flash chromatography (50 to 100% EtOAc in hexane), the title product as a white solid (3.20 g).

$^1$H NMR (CD$_3$COCD$_3$) δ3.10 (3H, s), 3.95 (3H, s), 4.65 (2H, s), 7.60 (2H, d), 7.96 (2H, d), 8.20 (4H, q).

Step 3

Cis,trans 4-(1-Chloro-3-oxo-2-(4-(methylsulfonyl) phenyl)-1-propenyl)benzoic acid methyl ester To a solution of 4-(1-oxo-2-((4-methylsulfonyl)phenyl) ethyl) benzoic acid (1.70 g) in 1,2-dichloroethane (15.0 mL) were added the Vilsmeier reagent 3.3 M (6.2 mL) and DMAP (0.624 g). The resulting mixture was heated at 80° C. for 4 h. The reaction mixture was then extracted with 25% aqueous solution of NH$_4$OAc and EtOAc. After drying over Na$_2$SO$_4$ and evaporation the title compound was obtained as an oil and used as such for the next step.

Step 4

5-(4-(Methoxycarbonyl)phenyl)-4-(4-(methylsulfonyl)phenyl)thiophene-2-carboxylic acid methyl ester Prepared from 4-(1-chloro-3-oxo-2-(4-methylsulfonyl) phenyl)-1-propenyl)benzoic acid methyl ester as for Example 1, Step 3.

$^1$H NMR (CD$_3$COCD$_3$) δ3.13 (3H, s), 3.85 and 3.92 (6H, 2s), 7.50 (2H, d), 7.55 (2H, d), 7.90 (2H, d), 7.92 (1H, s), 7.92 (2H, d).

Step 5

5-(4-(Carboxyphenyl)-4-(4-(methyl)sulfonyl)phenyl) thiophene-2-carboxylic acid

Prepared from 5-(4-(methoxycarbonyl)phenyl)-4-(4-(methyl)sulfonyl)phenyl) thiophene-2-carboxylic acid methyl ester as for Example 2, Step 1.

¹H NMR (CD₃COCD₃) δ3.15 (3H, s), 7.50 (2H, d), 7.62 (2H, d), 7.95 (2H, d), 7.98 (1H, s), 8.05 (2H, d).
Anal calcd. for $C_{19}H_{14}O_6S_2 \cdot 0.1 H_2O$: C, 56.46; H, 3.51.
Found: C, 56.18; H, 3.51.

EXAMPLE 6

4-(4-Fluorophenyl)-2-methyl-5-(4-(methylsulfonyl)phenyl)thiazole

Step 1

1-(4-Fluorophenyl)-2-(4-(methylsulfonyl)phenyl)ethanone

To 1-(4-Fluorophenyl)-2-(4-(methylthio)phenyl)ethanone of Example 1, Step 1 (17.9 g) in a solution of CH₂Cl₂-MeOH (272.0 mL/27.0 mL) at 0° C. was added MPPM (28.0 g). The cooling bath was then removed and the reaction mixture stirred at r.t. for 1 h. At 0° C., additional MPPM (28.0 g) was added and the reaction mixture kept for 1.5 h at r.t. The insoluble material was filtered followed by evaporation of the solvents, the residue was then extracted with CH₂Cl₂-NaHCO₃. After evaporation in vacuo, the resulting solid was washed with ether-hexane (1:1) and filtered to provide the title compound 16.8 g.

¹H NMR (CD₃COCD₃) δ3.13 (3H, s), 3.58 (2H, s), 7.29 (2H, t), 7.55 (2H, d), 7.88 (2H, d), 8.20 (2H, dd).

Step 2

2-Bromo-1-(4-fluorophenyl)-2-(4-(methylsulfonyl)phenyl)ethanone

To 1-(4-Fluorophenyl)-2-(4-(methylsulfonyl)phenyl)ethanone (1.00 g) in CH₂Cl₂ containing CHCl₃ (1.0 mL) and CCl₄ (1.0 mL) was added bromine (0.614 g). After shining light for 1 h, the reaction was quenched with Na₂S₂O₄, extracted with CH₂Cl₂, dried over Na₂SO₄ and evaporated to yield the title compound which was used as such for the next step (1.10 g).

¹H NMR (CD₃COCD₃) δ3.10 (3H, s), 7.05 (1H, s), 7.30 (2H, t), 7.87 (2H, d), 7.95 (2H, d), 8.25 (2H, dd).

Step 3

4-(4-Fluorophenyl)-2-methyl-5-(4-(methylsulfonyl)phenyl)thiazole

To 2-bromo-1-(4-fluorophenyl)-2-(4-(methylsulfonyl)phenyl)ethanone (1.10 g) in ethanol (15.0 mL) were added thioacetamide (0.266 g) and pyridine (0.300 mL). After refluxing for 2 h, the reaction mixture was extracted with EtOAc, 25% NH₄OAc and purified by flash chromatography (50% EtOAc in hexane then 90% Et₂O in hexane) to yield the title compound (0.320 g).

¹H NMR (CD₃COCD₃) δ2.72 (3H, s), 3.15 (3H, s), 7.09 (2H, t), 7.52 (2H, dd), 7.60 (2H, d), 7.92 (2H, d).
Anal. calcd. for $C_{17}H_{14}FNO_2S_2$: C, 58,78; H, 4.03; N, 4.03.
Found: C, 58.71, H, 4.17; N, 3.85.

EXAMPLE 7

2-(4-Fluorophenyl)-3-(4-methylsulfonyl)phenyl)-2-cyclopenten-1-one

Step 1

1-(4-Fluorophenyl)-5-hexen-2-one

To a suspension of 14.6 g (80 mmol) of CdCl₂ in 200 mL of ether cooled to 0° C. was added 115 mL of 1.3 M solution of 3-butene-1-magnesium bromide dropwise. The mixture was refluxed for 1 h and ether was then removed by distillation. Benzene (500 mL) was introduced, followed by a solution of 17.5 g (100 mmol) 4-fluorophenylacetyl chloride. After refluxing for 1 h, the reaction mixture was quenched with 200 mL of saturated aqueous NH₄Cl, 50 mL of 1 N HCl, and extracted with 200 mL of 1:1 hexane/EtOAC. The organic phase was dried over MgSO₄ and concentrated. The residue was purified by flash chromatography eluted with 4:1 hexane/EtOAc to give 15 g of the title product.

¹H NMR (CDC₃) δ2.40 (2H, t), 2.53 (2H, t), 3.63 (2H, s), 4.90–4.98 (2H, m), 5.67–5.78 (1H, m), 6.98 (2H, t), 7.13 (2H, m).

Step 2

1-(4-Fluorophenyl)-5-oxo-2-pentanone

A solution of 14 g of 1-(4-fluorophenyl)-5-hexen-2-one in 200 mL of 3:1 CH₂Cl₂/MeOH was cooled to −78° C. and treated with excess ozone. The resulting mixture was treated with 15 g of triphenylphosphine and stirred at room temperature for 1 h. The reaction mixture was concentrated and flash chromatographed with 3:1 hexane/EtOAc to give 8 g of the title ketoaldehyde.

¹H NMR (CDCl₃) δ2.72 (4H, s), 3.71 (2H, s), 6.99 (2H, t), 7.14 (2H, m), 9.73 (1H, s).

Step 3

2-(4-Fluorophenyl)-2-cyclopenten-1-one

A solution of 8 g of 1-(4-fluorophenyl)-5-oxo-2-pentanone in 300 mL of MeOH was treated with 2 g of NaOMe. The mixture was stirred for 2 h and then quenched with 5 mL of HOAc. The solvent was evaporated and the residue purified by flash chromatography, eluting with 3:1 hexane/EtOAc to give 7 g of the title product.

¹H NMR (CDCl₃) δ2.57 (2H, m), 2.68 (2H, m), 7.04 (2H, J=8.8 Hz, t), 7.67 (2H, J=8.8, 5.5 Hz, dd), 7.77 (1H, m).

Step 4

1-(4-(Methylthio)phenyl)-2-(4-fluorophenyl)-2-cyclopenten-1-ol

To a solution of 3.86 g (19 mmol) of 4-bromothioanisole in 90 mL of Et₂O cooled at −78° C., was added 22 niL of 1.7 M solution of t-BuLi in pentane (38 mmol) dropwise. The reaction mixture was stirred for 15 min at −78° C. and a solution of 2.23 g of 2-(4-Fluorophenyl)-2-cyclopenten-1-one in 10 mL of Et₂O was added. After stirring for 15 min at −78° C., the reaction mixture was warmed to 0° C., and quenched with 50 mL of sat. NH₄Cl. The product was extracted with 100 mL EtOAc, dried over Na₂SO₄, and purified by flash chromatography, eluted with 4:1 hexane/EtOAc to give 3.4 g of the desired product.

¹H NMR (CDCl₃) δ2.12 (1H, s), 2.34 (2H, m), 2.44 (3H, s), 2.45–2.52 (1H, m), 2.56–2.65 (1H, m), 6.37 (1H, m), 6.84 (2H, J=8.7 Hz, t), 7.17 (2H, J=8.3 Hz, d), 7.24–7.33 (4H, m).

Step 5

2-(4-Fluorophenyl)-3-(4-(methylthio)phenyl)-2-cyclopenten-1-one

To a suspension of PCC (4.5 g, 20.9 mmol) and 10 g of anhydrous 4 Å molecular sieves in 150 mL of CH₂Cl₂ was added a solution of 2.2 g (7.3 mmol) of ₁-(4-(methylthio)phenyl)-2-(4-fluorophenyl)-2-cyclopenten-1-ol in 20 mL CH₂Cl₂. The mixture was stirred for 1 h at r.t. and then diluted with 300 mL of Et$_2$O. After filtration and concentration, the residue was flash chromatographed with 2:1 hexane/EtOAc to give 1.5 g of the title product.

$^1$H NMR (CDCl$_3$) δ2.45 (3H, s), 2.68 (2H, m), 3.00 (2H, m), 7.02 (2H, J=8.6 Hz, t), 7.11 (2H, J=8.6 Hz, d), 7.15–7.23 (4H, m).

Step 6

2-(4-Fluorophenyl)-3-(4-(methylsulfonyl)phenyl)-2-cyclopenten-1-one

To a solution of 50 mg (0.17 mmol) of 2-(4-Fluorophenyl)-3-(4-metylthio)phenyl)-2-cyclopenten-1-one in 8 mL of 10:1 CH$_2$Cl$_2$/MeOH was added 124 mg (0.2 mmol) of MPPM. The reaction mixture was stirred at room temperature for 2 h and then diluted with 10 mL of 1:1 hexane/EtOAc. After filtration and concentration, the residue was purified by flash chromatography eluted with 2:1 EtOAc/hexane to give 45 mg of the title product.

$^1$H NMR (acetone-d$_6$) δ2.67 (2H, m), 3.14 (3H, s), 3.16 (2H, m), 7.05–7.10 (2H, m), 7.20–7.25 (2H, m), 7.63 (2H, d), 7.93 (2H, d).

EXAMPLE 8

4-(4-(Methylsulfonyl)phenyl)-5-(4-fluorophenyl)-isothiazole

To a solution of 338 mg (1 mmol) of cis,trans 3-chloro-3-(4-fluorophenyl)-2-(4-(methylsulfonyl)phenyl)propenal in 5 mL of acetone was added 230 mg (3 mmol) of NH$_4$SCN. The reaction mixture was refluxed for 3 h, and then quenched with 20 mL of saturated NaHCO$_3$. The product was extracted with 100 mL of EtOAc, dried over Na$_2$SO$_4$, concentrated and purified by flash chromatography eluted with 3:2 hexane/EtOAc to give 250 mg of the title product.

$^1$H NMR (CDCl$_3$) δ8.57 (1H, s), 7.93 (3H, d), 7.50 (2H, d), 7.30 (2H, t), 7.08 (2H, t).

EXAMPLE 9

3-(4-Fluorophenyl)-4-(4-(methylsulfonyl)phenyl)-2-(5H)-furanone

Step 1

2-Bromo-1-(4-(methylsulfonyl)phenyl)ethanone

A solution of 197 g of 4-(Methylthio)acetophenone (ref: JACS, 1952, 74, p. 5475) in 700 mL of MeOH and 350 mL of CH$_2$Cl$_2$ was added 881 g of MMPP over a period of 30 min. After 3 h at room temperature the reaction mixture was filtered and the filtrate was washed with 2 L of saturated aqueous solution of NaHCO$_3$ and 1 L of brine. The aqueous phase was further extracted with 2 L of CH$_2$Cl$_2$. The combined extracts was dried over Na$_2$SO$_4$ concentrated to give 240 g of 4-(methylsulfonyl)acetophenone as a white solid.

To a cooled (−5° C.) solution of 174 g of 4-(methylsulfonyl)acetophenone in 2.5 L of CHCl$_3$ was added 20 mg of AlCl$_3$, followed by a solution of 40 mL of Br$_2$ in 300 mL CHCl$_3$. The reaction mixture was then treated with 1.5 L of water and the CHCl$_3$ was separated. The aqueous layer was extracted with 1 L of EtOAc. The combined extracts was dried over Na$_2$SO$_4$ and concentrated. The crude product was recystalized from 50/50 EtOAc/hexane to give 210 g of 2-bromo-1-(4-(methylsulfonyl)phenyl)ethanone as a white solid.

Step 2

To the product of Step 1 (216 mg) dissolved in acetonitrile (4 mL) was added Et$_3$N (0.26 mL), followed by 4-fluorophenylacetic acid (102 mg). After 1.5 h at room temperature 0.23 mL of DBU was added. The reaction mixture was stirred for another 45 min and then treated with 5 mL of 1N HCl. The product was extracted with EtOAc, dried over Na$_2$SO$_4$ and concentrated. The residue was purified by flash chromatography (40% EtOAc in hexane) to yield 150 mg of the title compound as a solid.

$^1$H NMR (CD$_3$COCD$_3$) δ3.15 (3H, s), 5.36 (3H, s), 7.18 (2H, J=8.9 Hz, t), 7.46 (2H, m), 7.7 (2H, J=8.65 Hz, d), 7.97 (2H, J=8.68, d).

EXAMPLE 10

3-(4-Fluorophenyl)-4-(4-(aminosulfonyl)phenyl)-2-(2H)-furanone $^1$H NMR (CD$_3$COCD$_3$) δ5.34 (2H, s), 6.67 (2H, bd), 7.18 (2H, m), 7.46 (2H, m), 7.61 (2H, m), 7.90 (2H, m).

M.P. 187–188° C. (d).

EXAMPLE 11

3-(4-Fluorophenyl)-4-(4-(methylsulfonyl)phenyl) furan

Step 1

Using the product of Example 10, (0.2 g) in THF (5 mL) and toluene (3 mL) was added slowly at −78° C. a solution of DIBAL (0.72 mL, 1M in toluene). After 15 min, the solution was warmed up to 0° C. for another 15 min. This mixture was then poured into a chilled aqueous solution of sodium potassium tartrate and EtOAc. The organic layer was stirred for 0.5 h with a few crystals of camphor sulfonic acid. This solution was then concentrated and purified by flash chromatography to yield the title compound.

$^1$H NMR (CDCl$_3$)_3.1 (3H, s), 7.02 (2H, J=8.9, t), 7.18 (2H, m), 7.4 (2H, J=8.8 Hz, d), 7.58 (1H, s), 7.68 (1H, s), 7.85 (2H, J=8.8 Hz, d)

EXAMPLE 12

5,5-Dimethyl-3-(4-fluorophenyl)4-(4-methylsulfonylphenyl)-2-(5H)-furanone

Step 1

Methyl 2-trimethylsilyloxyisobutyrate

To a solution of 1.2 mL (10.4 mmol) of methyl 2-hydroxyisobutyrate in 50 mL of CH$_2$Cl$_2$ were added 1.2 g (17.6 mmol) of imidazole and 2.1 mL (16.6 mmol) of TMSCl. The mixture was stirred at r.t. for 1.5 h and quenched with 20 mL of H$_2$O. The organic layer was dried over MgSO$_4$, concentrated and passed through a short plug of silica gel eluted with 9:1 hexane/EtOAc. Evaporation of solvent afforded 1.27 g of the title compound as a colorless oil.

$^1$H NMR (CD$_3$COCD$_3$) δ0.08 (9H, s), 1.38 (6H, s), 3.67 (3H, s).

Step 2

2-Trimethylsilyloxy-4'-(methylthio) isobutyrophenone

A solution of 204 mg (1.0 mmol) of 4-bromothioanisole in 2.5 mL of THF was cooled to −78° C. and treated with 0.42 mL of 2.5 M n-BuLi solution in hexane. After stirring at −78° C. for 1 h, a solution of 380 mg (2.0 mmol) of methyl 2-trimethylsilyloxyisobutyrate in 2 mL of THF was added. The mixture was stirred at −78° C. for 2 h and then quenched with NH₄OAc buffer. The product was extracted with EtOAc, dried over MgSO₄ and concentrated. The residue was purified by flash chromatography, eluting with 19:1 hexane/EtOAc to give 95 mg of the title product.

$^1$H NMR (CD$_3$COCD$_3$) δ0.05 (9H, s), 1.52 (6H, s), 2.53 (3H, s), 7.33 (2H, d), 8.12 (2H, d).

Step 3

2-Hydroxy-4'-(methylthio)isobutyrophenone

To a solution of 40 mg (0.14 mmol) of 2-trimethylsilyloxy-4'-(methylthio)isobutyrophenone in 2 mL THF was added 0.2 mL of 1 M n-Bu₄NF in THF. The resulting mixture was stirred for 30 min and then quenched with 10 mL of NH₄OAc buffer. The product was extracted with EtOAc, dried over MgSO₄ and concentrated. The residue was purified by flash chromatography, eluting with 4:1 hexane/EtOAc to give 25 mg of the title product.

$^1$H NMR (CD$_3$COCD$_3$) δ1.50 (6H, s), 2.54 (3H, s), 4.68 (1H, s), 7.30 (2H, d), 8.15 (2H, d).

Step 4

2-(4-Fluorophenylacetoxy)-4'-(methylthio)isobutyrophenone

To a solution of 72 mg (0.34 mmol) 2-hydroxy-4'(methylthio)isobutyrophenone in 1.7 mL of CH₂Cl₂ were added 0.2 mL of pyridine and 140 mg (0.81 mmol) of 4-fluorophenylacetyl chloride. The mixture was stirred at room temperature overnight and then quenched with NH₄OAc buffer. The product was extracted with EtOAc, dried over MgSO₄ and concentrated. The crude product was purified by flash chromatography eluting with 8:1 hexane/EtOAc to give 95 mg of the title product.

$^1$H NMR (CD$_3$COCD$_3$) δ1.62 (3H, s), 1.67 (3H, s), 2.48 (3H, s), 3.79 (2H, s), 7.0–7.3 (6H, m), 7.78 (2H, d).

Step 5

5,5-Dimethyl-3-(4-fluorophenyl-4-(4-methylthiophenyl)-2-(5H)-furanone

To a solution of 95 mg of 2-(4-fluorophenylacetoxy)-4'-(methylthio)-isobutyrophenone in 4 mL of CH₂Cl₂ was added 0.2 mL of 1,8-diazabicyclo(5.4.0)undec-7-ene. The mixture was stirred for 4 h and diluted with NH₄OAc buffer. The product was extracted with EtOAc, dried over MgSO₄ and concentrated. The residue was purified by flash chromatography, eluting with 20:1 toluene/EtOAc to give 75 mg of the title product.

$^1$H NMR (CD$_3$COCD$_3$) δ1.58 (6H, s), 2.50 (3H, s), 7.03 (2H, dd), 7.25–7.35 (4H, m), 7.41 (2H, dd).

Step 6

5,5-Dimethyl-3-(4-fluorophenyl)-4-(4-methylsulfonylphenyl)-2-(5H)-furanone

To a solution of 81 mg of 5,5-dimethyl-3-(4-fluorophenyl)-4-(4-methyl-thiophenyl)-2-oxo-2H-dihydrofuran in 1.8 mL of CH₂Cl₂ and 0.2 mL of MeOH was added 250 mg of MPPM. The reaction mixture was stirred at room temperature for 1 h and then quenched with aqueous NaHCO₃. The product was extracted with EtOAc, dried over MgSO₄ and concentrated. The crude product was purified by flash chromatography eluting with 1:1 hexane/EtOAc to give 73 mg of the title product.

$^1$H NMR (CD$_3$COCD$_3$) δ1.62 (6H, s), 3.15 (3H, s), 7.02 (2H, dd), 7.40 (2H, dd), 7.65 (2H, d), 8.03 (2H, d).

EXAMPLE 13

2-((4-aminosulfonyl)phenyl)-3-(4-fluorophenyl)thiophene $^1$H NMR (CD$_3$COCD$_3$) δ6.60 (2H, bs), 7.12 (2H, t), 7.25 (1H, d), 7.35 (2H, m), 7.45 (2H, d), 7.65 (1H, d), 7.85 (2H, d).

Analysis calculated for C$_{16}$H$_{12}$FNS$_2$O$_2$ C, 57.65; H, 3.60; N, 4.20

Found: C, 57.55; H, 3.79; N, 4.03

EXAMPLE 14

3-(4-(Trifluoroacetylaminosulfonyl)phenyl)-2-(4-fluorophenyl)thiophene $^1$H NMR (300 MHz, CD$_3$COCD$_3$) δ7.15 (2H, t), 7.30 (3H, m), 7.45 (2H, d), 7.65 (1H, d), 7.95 (2H, d).

EXAMPLE 15

3-(2,4-Difluorophenyl)-4-(4-(methylsulfonyl)phenyl)-2-(5H)-furanone

Analysis calculated for C$_{17}$H$_{12}$F$_2$O$_4$S C, 58.28; H, 3.45; S, 9.15.

Found: C, 58.27; H, 3.50; S, 9.27.

EXAMPLE 16

3-(3,4-Difluorophenyl)-4-(4-(methylsulfonyl)phenyl)-2-(5H)-furanone

To a solution of 3,4-difluorophenylacetic acid (ALDRICH CHIMICAL) (10 g) and 2-bromo-1-(4-(methylsulfonyl)phenyl)ethanone (Example 9, Step 1) (17.3 g) in acetonitrile (200 mL) at room temperature was added slowly triethylamine (20.2 mL). After 1 h at room temperature, the mixture was cooled in an ice bath and treated with 17.4 mL of DBU. After 2 h at 0° C., the mixture was treated with 200 mL of 1N HCl and the product was extracted with EtOAc, dried over Na$_2$SO$_4$ and concentrated. The residue was applied on top of a silica gel plug (sintered glass funnel) eluted with 75% EtOAc/hexane, giving after evaporation of the solvent and swish in ethyl acetate, 10 g of the title compound.

Analysis calculated for C$_{17}$H12F$_2$O$_4$S C, 58.28; H, 3.45; S, 9.15.

Found: C, 58.02; H, 3.51; S, 9.35.

EXAMPLE 17

3-(2,6-Difluorophenyl)-4-(4-(methylsulfonyl)phenyl)-2-(5H)-furanone

Analysis calculated for C$_{17}$H$_{12}$F$_2$O$_4$S C, 58.28; H, 3.45; S, 9.15.

Found: C, 58.18; H, 3.50; S, 9.44.

EXAMPLE 18

3-(2,5-Difluorophenyl)-4-(4-(methylsulfonyl)phenyl)-2-(5-furanone

Analysis calculated for C$_{17}$H$_{12}$F$_2$O$_4$S C, 58.28; H, 3.45; S, 9.15.

Found: C, 58.89; H, 3.51; S, 9.11.

EXAMPLE 19

3-(3,5-Difluorophenyl)-4-(4-(methylsulfonyl)phenyl)-2-(5H)-furanone

Analysis calculated for C$_{17}$H$_{12}$F$_2$O$_4$S C, 58.28; H, 3.45; S, 9.15.

Found: C, 58.27; H, 3.62; S, 9.32.

EXAMPLE 20

3-(4-Bromophenyl)-4-(4-(methylsulfonyl)phenyl)-2-(5H)-furanone

Analysis calculated for C$_{17}$H$_{13}$BrO$_4$S C, 51.94; H, 3.33; S, 8.16.

Found: C, 51.76; H, 3.42; S, 8.21.

EXAMPLE 21

3-(4-Chlorophenyl)-4-(4-(methylsulfonyl)phenyl)-2-(5H)-furanone $^1$H NMR (300 MHz, CDCl$_3$) δ7.93 (2H, d), 7.49 (2H, d), 7.35 (4H, m), 5.16 (2H, s), 3.06 (3H, s)

EXAMPLE 22

3-(4-Methoxyphenyl)4-(4-(methylsulfonyl)phenyl)-2-(5H)-furanone

Analysis calculated for C$_{18}$H$_{16}$O$_5$S C, 62.78 H, 4.68; S, 9.31.

Found: C, 62.75; H, 4.72; S, 9.39.

EXAMPLE 23

3-(Phenyl)-4-(4-(methylsulfonyl)phenyl)-2-(5H)-furanone

To a solution of phenylacetic acid (27.4 g, 201 mmol) and 2-bromo-1-(4-(methylsulfonyl)phenyl)ethanone (Example 9, Step 1) (60 g, 216 mmol, 1.075 eq.) in acetonitrile (630 mL) at 25° C. was added slowly triethylamine (30.8 mL, 1.1 eq.). The mixture was stirred for 20 min. at room temperature and then cooled in an ice bath. DBU (60.1 mL, 3 eq.) was slowly added. After stirring for 20 min. in the ice bath, the reaction was complete and the mixture was acidified with 1N HCl (color changes from dark brown to yellow). Then 2.4 L of ice and water were added, stirred for a few minutes, then the precipitate was filtered and rinsed with water (giving 64 g of crude wet product). The solid was dissolved in 750 mL of dichloromethane (dried over MgSO$_4$, filtered) and 300 g of silica gel was added. The solvent was evaporated to near dryness (silica gel a bit sticky) and the residue was applied on top of a silica gel plug (sintered glass funnel) eluted with 10% EtOAc/CH$_2$Cl$_2$, giving after evaporation of the solvent and swish in ethyl acetate, 36.6 g (58%) of the title compound.

Analysis calculated for C$_{17}$H$_{14}$O$_4$S C, 64.95; H, 4.49; S, 10.20.

Found: C, 64.63; H, 4.65; S, 10.44.

EXAMPLE 24

3-(2-Chlorophenyl)-4-(4-(methylsulfonyl)phenyl)-2-(5H)-furanone

Analysis calculated for C$_{17}$H$_{13}$ClO$_4$S C, 58.54; H, 3.76; S, 9.19.

Found: C, 58.59; H, 3.80; S, 9.37.

EXAMPLE 25

3-(2-Bromo-4-fluorophenyl)-4-(4-(methylsulfonyl)phenyl)-2-(5H)-furanone

Analysis calculated for C$_{17}$H$_{12}$BrFO$_4$S C, 49.75; H, 2.93. Found: C, 49.75; H, 3.01.

EXAMPLE 26

3-(2-Bromo-4-Chlorophenyl)-4-(4-(methylsulfonyl)phenyl-2-(5)-furanone

1H NMR (300 MHz, acetone-d$_6$) δ7.95 (2H, d), 7.85 (1H, d), 7.63 (2H, dd), 7.55 (1H, dd), 7.45 (1H, dd), 5.50 (2H, s), 3.15 (3H, s)

EXAMPLE 27

3-(4-Chloro-2-fluorophenyl)-4-(4-(methylsulfonyl)phenyl)-2-(5H)-furanone $^1$H NMR (300 MHz, acetone-d$_6$) δ8.0 (2H, d), 7.70 (2H, d), 7.50–7.30 (3H, m), 5.35 (2h, s), 3.15 (3H, s)

EXAMPLE 28

3-(3-Bromo-4-fluorophenyl)-4-(4-(methylsulfonyl)phenyl)-2-(5H)-furanone

Analysis calculated for C$_{17}$H$_{12}$BrFO$_4$S C, 49.75; H, 2.93. Found: C, 49.44; H, 2.98.

EXAMPLE 29

3-(3-Chlorophenyl)-4-(4-(methylsulfonyl)phenyl)-2-(5H)-furanone

Analysis calculated for C$_{17}$H$_{13}$ClO$_4$S C, 58.54; H, 3.76. Found: C, 58.29; H, 3.76.

EXAMPLE 30

3-(2-Chloro-4-fluorophenyl)-4-(4-(methylsulfonyl)phenyl)-2-(5H)-furanone

Analysis calculated for C$_{17}$H$_{12}$ClFO$_4$S C, 55.67; H, 3.30. Found: C, 55.67; H, 3.26.

EXAMPLE 31

3-(2,4-Dichlorophenyl)-4-(4-(methylsulfonyl)phenyl)-2-(5H)-furanone

Analysis calculated for C$_{17}$H$_{12}$Cl$_2$O$_4$S C, 53.28; H, 3.16; S, 8.37.

Found: C, 52.89; H, 3.23; S, 8.58.

EXAMPLE 32

3-(3,4-Dichlorophenyl)-4-(4-(methylsulfonyl)phenyl)-2-(5H)-furanone

Analysis calculated for C$_{17}$H$_{12}$Cl$_2$O$_4$S C, 53.28; H, 3.16; S, 8.37.

Found: C, 53.07; H, 3.32; S, 8.51.

EXAMPLE 33

3-(2,6-Dichlorophenyl)-4-(4-(methylsulfonyl)phenyl)-2-(5H)-furanone

Analysis calculated for C$_{17}$H$_{12}$Cl$_2$O$_4$S C, 53.28; H, 3.16; S, 8.37.

Found: C, 52.99; H, 3.22; S, 8.54.

EXAMPLE 34

3-(3-Chloro-4-fluorophenyl)-4-(4-methylsulfonyl)phenyl)-2-(5H)-furanone $^1$H NMR (300 MHz, acetone-d$_6$) d 8.0 (2H, d), 7.70 (2H, d), 7.60 (1H, d), 7.25–7.40 (2H, m), 5.35 (2H, s), 3.15 (3H, s)

EXAMPLE 35

3-(4-Trifluoromethylphenyl)-4-(4-(methylsulfonyl)phenyl)-2-(5H-furanone $^1$H NMR (CD$_3$COCD$_3$) δ8.10 (2H, d), 7.82–7.93 (4H, m), 7.75 (2H, d), 5.55 (2H, s), 3.30 (3H, s)

EXAMPLE 36

3-(3-Fluoro-4-methoxyphenyl)-4-(4-(methylsulfonyl)phenyl)-2-(5H)-furanone

Analysis calculated for $C_{18}H_{15}FO_5S$ C, 59.66; H, 4.17. Found: C, 59.92; H, 4.37.

EXAMPLE 37

3-(3-Chloro-4-methoxyphenyl)-4-(4-(methylsulfonyl)phenyl)-2-(5H)-furanone

Analysis calculated for $C_{18}H_{15}ClO_5S$ C, 57.07; H, 3.99. Found: C, 57.29; H, 4.15.

EXAMPLE 38

3-(3-Bromo-4-methoxyphenyl)-4-(4-(methylsulfonyl)phenyl)-2-(5H)-furanone

Analysis calculated for $C_{18}H_{15}BrO_5S$ C, 51.08; H, 3.57. Found: C, 51.38; H, 3.62.

EXAMPLE 39

3-(2-Fluorophenyl)-4-(4-(methylsulfonyl)phenyl)-2-(5H)-furanone

Analysis calculated for $C_{17}H_{13}FO_4S$ C, 61.44; H, 3.94. Found: C, 61.13; H, 3.85.

EXAMPLE 40

3-(4-Methylthiophenyl)-4-(4-(methylsulfonyl)phenyl)-2-(5H)-furanone $^1$H NMR (300 MHz, acetone-$d_6$) d 8.0 (2H, d), 7.70 (2H, d), 7.35 (2H, d), 7.25 (2H, d), 5.35 (2H, s), 3.15 (3H, s), 2.55 (3H, s)

EXAMPLE 41

3-(3-Fluorophenyl-4-(4-methylsulfonyl)phenyl)-2-(5H)-furanone $^1$H NMR (300 MHz, CDCl3) d 7.93 (2H, d), 7.49 (2H, d), 7.35 (1H, m), 7.12 (3H, m), 5.18 (2H, s), 3.06 (3H, s)

EXAMPLE 42

3-(2-Chloro-6-fluorophenyl)-4-(4-(methylsulfonyl)phenyl)-2-(5H)-furanone $^1$H NMR (300 MHz, acetone-d6), d 8.0 (2H, d), 7.70 (2H, d), 7.55–7.65 (1H, m), 7.40 (1H, d), 7.30 (1H, m), 5.60 (2H, s), 3.15 (3H, s)

EXAMPLE 43

3-(3-Bromo-4-methylphenyl)-4-(4-(methylsulfonyl)phenyl)-2-(5H)-furanone

Analysis calculated for $C_{18}H_{15}BrO_4S$ C, 53.08; H, 3.71. Found: C, 53.06; H, 3.83.

EXAMPLE 44

3-(4-Bromo-2-fluorophenyl)-4-(4-(methylsulfonyl)phenyl)-2-(5H)-furanone

Analysis calculated for $C_{17}H_{12}BrFO_4S$ C, 49.65; H, 2.94. Found: C, 49.76; H, 3.00.

EXAMPLE 45

3-(3,4-Dibromophenyl)-4-(4-(methylsulfonyl)phenyl)-2-(5H)-furanone $^1$H NMR (300 MHz, acetone-$d_6$) $\delta$8.0 (2H, d), 7.80 (1H, d), 7.75 (3H, m), 7.25 (1H, d), 5.35 (2H, s), 3.15 (sH, s)

EXAMPLE 46

3-(4-Chloro-3-fluorophenyl)-4-(4-(methylsulfonyl)phenyl)-2-(5H)-furanone

Analysis calculated for $C_{17}H_{12}ClFO_4S$ C, 55.67; H, 3.30. Found: C, 55.45; H, 3.30.

EXAMPLE 47

3-(4-Bromo-3-fluorophenyl)-4-(4-(methylsulfonyl)phenyl)-2-(5H)-furanone

Analysis calculated for $C_{17}H_{12}BrFO_4S$ C, 49.66; H, 2.94; S, 7.80. Found: C, 49.79; H, 3.01; S, 7.51.

EXAMPLE 48

3-(4-Bromo-2-chlorophenyl)-4-(4-(methylsulfonyl)phenyl)-2-(5H)-furanone

Analysis calculated for $C_{17}H_{12}BrClO_4S$ C, 47.74; H, 2.83; S, 7.50. Found: C, 47.92; H, 2.84; S, 7.42.

EXAMPLE 49

3-(2-Naphthyl)-4-(4-(methylsulfonyl)phenyl)-2-(5H)-furanone

Analysis calculated for $C_{21}H_{16}O_4S$ C, 69.22; H, 4.43. Found: C, 69.22; H, 4.46.

EXAMPLE 50

3-(7-Quinolinyl)-4-(4-(methylsulfonyl)phenyl)-2-(5)-furanone

Analysis calculated for $C_{20}H_{15}NO_4S$ C, 65.74; H, 4.14; N, 3.83.

Found: C, 65.34; H, 4.40; N, 3.80.

M.S. (DCI, $CH_4$) calculated for $M^+$, 365 Found for $M^++1$, 366

EXAMPLE 51

3-(3,4-Dichlorophenyl)-4-(4-(aminosulfonyl)phenyl)-2-(2H)-furanone $^1$H NMR (400 MHz, $CD_3COCD_3$) $\delta$7.92 (2H, dd), 7,64 (3H, dm), 7.60 (1H, dd), 7.32 (1H, dd), 6.70 (1H, bs), 5.38 (2H, s)

EXAMPLE 52

3-(3,4-Difluorophenyl)-4-(4-(aminosulfonyl)phenyl)-2-(2H)-furanone $^1$H NMR (400 MHz, $CD_3COCD_3$) $\delta$7.92 (2H, dd), 7,64 (2H, dd), 7.30–7.45 (2H, m), 7.22 (1H, m), 6.68 (2H, bs), 5.37 (2H, s)

EXAMPLE 53

3-(3-Chloro-4-methoxyphenyl)-4-(4-(aminosulfonyl)phenyl)-2-(2H)-furanone

Analysis calculated for $C_{17}H_{14}ClNO_5S$ C, 53.76; H, 3.72, N, 3.69.

Found: C, 53.32; H, 3.84, N, 3.59.

M.S. (DCI, CH$_4$) calculated for M$^+$, 379 Found for M$^+$+1, 380.

EXAMPLE 54

3-(3-Bromo-4-methoxyphenyl)-4-(4-(aminosulfonyl)phenyl)-2-(2H)-furanone

Analysis calculated for C$_{17}$H$_{14}$BrNO$_5$S C, 48.13; H, 3.33, N, 3.30.

Found: C, 48.26; H, 3.40, N, 3.28.

M.S. (DCI, CH$_4$) calculated for M$^+$, 423 Found for M$^+$+1, 424.

What is claimed is:

1. A compound which is 3-phenyl-4-(4-(methylsulfonyl)phenyl)-2-(5H)-furanone.

2. A method of treating an inflammatory disease in a human patient in need of such treatment comprising administering a non-toxic therapeutically effective amount of 3-phenyl-4-(4-(methylsulfonyl)phenyl)-2-(5H)-furanone and a pharmaceutically acceptable carrier.

3. A method of treating a cyclooxygenase-2 mediated disease in a human patient in need of such treatment comprising administering a non-toxic therapeutically effective amount of 3-phenyl-4-(4-(methylsulfonylphenyl)-2-(5H)-furanone and a pharmaceutically acceptable carrier.

4. A method according to claim 2 of treating arthritis in a human patient in need of such treatment comprising administering a non-toxic therapeutically effect amount of 3-phenyl-4-(4-(methylsulfonyl)phenyl)-2-(5H)-furanone and a pharmaceutically acceptable carrier.

5. A method according to claim 2 of treating rheumatoid arthritis in a human patient in need of such treatment comprising administering a non-toxic therapeutically effective amount of 3-phenyl-4-(4-(methylsulfonyl)phenyl)-2-(5H)-furanone and a pharmaceutically acceptable carrier.

6. A method according to claim 2 of treating osteoarthritis in a human patient in need of such treatment comprising administering a non-toxic therapeutically effective amount of 3-phenyl-4-(4-(methylsulfonyl)phenyl)-2-(5H)-furanone and a pharmaceutically acceptable carrier.

7. A method according to claim 2 of treating pain in a human patient in need of such treatment comprising administering a non-toxic therapeutically effective amount of 3-phenyl-4-(4-(methylsulfonyl)phenyl)-2-(5H)-furanone and a pharmaceutically acceptable carrier.

8. A method according to claim 2 of treating fever in a human patient in need of such treatment comprising administering a non-toxic therapeutically effect amount of 3-phenyl-4-(4-(methylsulfonyl)phenyl)-2-(5H)-furanone and a pharmaceutically acceptable carrier.

9. A method according to claim 2 of treating dysmenorrhea in a human patient in need of such treatment comprising administering a non-toxic therapeutically effective amount of 3-phenyl-4-(4-(methylsulfonyl)phenyl)-2-(5H)-furanone and a pharmaceutically acceptable carrier.

10. A pharmaceutical compostion comprising 3-phenyl-4-(4-(methylsulfonyl)phenyl)-2-(5H)-furanone and a pharmaceutically acceptable carrier.

* * * * *